United States Patent
Skowronska-Krawczyk et al.

(10) Patent No.: US 10,632,211 B2
(45) Date of Patent: Apr. 28, 2020

(54) DEMETHYLATION TO TREAT EYE DISEASE

(71) Applicant: The Regents of the University of California, Oakland, CA (US)

(72) Inventors: Dorota Skowronska-Krawczyk, La Jolla, CA (US); Daniel Lee Chao, La Jolla, CA (US); Daniel Chen, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/424,974

(22) Filed: May 29, 2019

(65) Prior Publication Data
US 2019/0374653 A1    Dec. 12, 2019

Related U.S. Application Data

(60) Provisional application No. 62/716,554, filed on Aug. 9, 2018, provisional application No. 62/683,292, filed on Jun. 11, 2018.

(51) Int. Cl.
| | | |
|---|---|---|
| A61K 48/00 | (2006.01) | |
| A61K 31/706 | (2006.01) | |
| A61P 27/02 | (2006.01) | |
| A61K 9/00 | (2006.01) | |

(52) U.S. Cl.
CPC ......... *A61K 48/005* (2013.01); *A61K 9/0048* (2013.01); *A61K 31/706* (2013.01); *A61K 48/0075* (2013.01); *A61P 27/02* (2018.01)

(58) Field of Classification Search
CPC .................................................. A61K 48/005
See application file for complete search history.

(56) References Cited

U.S. PATENT DOCUMENTS

| | | |
|---|---|---|
| 7,135,464 B2 | 11/2006 | Joshi-Hangal et al. |
| 2005/0137124 A1 | 6/2005 | Castillejos |
| 2016/0051503 A1 | 2/2016 | Coffey |
| 2017/0035794 A1 | 2/2017 | Phiasivongsa et al. |
| 2017/0143848 A1 | 5/2017 | Calias et al. |
| 2018/0010141 A1 | 1/2018 | Petrie et al. |
| 2018/0135066 A9 | 5/2018 | Walsh et al. |

FOREIGN PATENT DOCUMENTS

| | | |
|---|---|---|
| CN | 102660576 B | 6/2014 |
| WO | 2005/030985 A2 | 4/2005 |
| WO | 2006/017278 A1 | 2/2006 |

OTHER PUBLICATIONS

Wei et al (Asia Pac J Ophthalmol (Phila). Jul.-Aug. 2013; 2(4): 269-274). (Year: 2013).*

(Continued)

*Primary Examiner* — Benjamin J Packard
(74) *Attorney, Agent, or Firm* — Eversheds Sutherland (US) LLP

(57) ABSTRACT

Methods for treating age-related eye diseases or conditions are provided. Methods for treating an age-related eye disease or condition in a subject by administering one or more demethylation compounds or agents are provided.

15 Claims, 15 Drawing Sheets

Specification includes a Sequence Listing.

(56) References Cited

OTHER PUBLICATIONS

Chen, D. (2018). The Role of ELOVL2 in Aging and Eye Disease. UC San Diego. ProQuest ID: Chen_ucsd_0033D_17183. Merritt ID: ark:/13030/m55x768z. Retrieved from https://escholarship.org/uc/item/7m4555h9). (Year: 2018).*

Agbaba et al., "Role of Stargardt-3 Macular Dystrophy Protein (ELOVL4) in the Biosynthesis of Very Long Chain Fatty Acids," PNQAS, 2008, 105(35):12843-12848.

Bacalini et al., "A Meta-Analysis on Age-Associated Changes in Blood DNA Methylation: Results from an Original Analysis Pipeline for Infinium 450k Data," Aging, 2015, 7(2):97-109.

Bazan et al., "Docosahexaenoic Acid Signalolipidomics in Nutrition: Significance in Aging, Neuroinflammation, Macular Degeneration, Alzheimer's, and Other Neurodegenerative Diseases," Annu. Rev., Nutr., 2011, 31:321-351.

Beatty et al., "The Role of Oxidative Stress in the Pathogenesis of Age-Related Macular Degeneration," Study of Ophthalmology, 2000, 45(2):115-134.

Cameron et al., "HTRA1 Variant Confers Similar Risks to Geographic Atrophy and Neovascular Age-Related Macular Degeneration," Cell Cycle, 2007, 6(9):1122-1125.

Crabb et al., "Drusen Proteome Analysis: An Approach to the Etiology of Age-Related Macular Degeneration," PNAS, 2002, 99(23):14682-14687.

Curcio et al., "Apolipoprotein B-containing Lipoproteins in Retinal Aging and Age-Related Macular Degeneration," Journal of Lipid Research, 2010, 51:451-467.

Garagnani et al., "Methylation of ELOVL2 Gene a a New Epigenetic Marker of Age," Aging Cell, 2012, 11:1132-1134.

Gross et al., "Methylome-Wide Analysis of Chronic HIV Infection Reveals Five-Year Increase in Biological Age and Epigenetic Targeting of HLA," Molecular Cell, 2016, 62:157-168.

Hannum et al., "Genome-Wide Methylation Profiles Reveal Quantitative Views of Human Aging Rates," Mol Cell., 2013, 49(2):359-367.

Harkewicz et al., "Essential Role of ELOVL4 Protein in Very Long Chain Fatty Acid Synthesis and Retinal Function," Journal of Biological Chemistry, 2012, 287(14):11469-11480.

Hollyfield et al., "Oxidative Damage-Induced Inflammation Initiates Age-Related Macular Degeneration," Nature Medicine, 2008, 14(2):194-198.

Shaw et al., "Complement Factor H Genotypes Impact Risk of Age-Related Macular Degeneration by Interaction with Oxidized Phospholipids," PNAS, 2012, 109(34):13757-13762.

Shaw et al., "Natural Antibodies with the T15 Idiotype May Act in Atherosclerosis, Apoptotic Clearance, and Protective Immunity," J. Clin. Invest., 2000, 105(12):1731-1740.

Sivaprasad et al., "The Complement System and Age-Related Macular Degeneration," Eye, 2006, 20:867-872.

Tikhonenko et al., "Remodeling of Retinal Fatty Acids in an Animal Model of Diabetes," Diabetes, 2010, 59:219-227.

PCT International Search Report and Written Opinion for PCT Application No. PCT/US2019/034289 dated Sep. 16, 2019 (17 pages).

Hagemann et al., "Azacytidine and Decitabine Induce Gene-Specific and Non-Random DNA Demethylation in Human Cancer Cell Lines," PLoS ONE, 2011, 6(3):e17388 (11 pages).

Marttila et al., "Ageing-Associated Changes in the Human DNA Methylome: Genomic Locations and Effects on Gene Expression," BMC Genomics, 2015, 16:179 (17 pages).

* cited by examiner

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gtaattccgt gatcaccgtc                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaataaata acagcagaag                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatatgctc atcattgtct                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacacatgt ctaccttcct                                                 20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgatttgcag gtccagccg                                                  19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagcgggtgg gtattcctg                                                  19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaggtgtgg acatctcttg                                                      20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgcaggagcg tacagaa                                                         17

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agctcctccg ctactc                                                          16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagcccttg gtcatc                                                          16

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taggcccaga tgtacaggaa                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccagaatgca ggcctagtaa                                                      20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggatcatg gaacatctaa                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagccatat tgagagcaga                                              20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccattggc aatgagcggt tc                                           22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggtctttgc ggatgtccac gt                                           22

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Pro Phe Gly Cys Leu Ile Phe Gln Ser Ser Tyr Met Met Thr Leu
1               5                   10                  15

Val

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcccctttg gctgtctcat cttccagtct tcctatatga tgacgctggt c           51

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
tttcccttcg gctggctcat cttccagtct tcctatatga tgacgttagt c            51

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Pro Phe Gly Trp Leu Ile Phe Gln Ser Ser Tyr Met Met Thr Leu
1               5                   10                  15

Val

<210> SEQ ID NO 21
<211> LENGTH: 299
<212> TYPE: PRT
<213> ORGANISM: Homo sapiens

<400> SEQUENCE: 21

Met Glu His Phe Asp Ala Ser Leu Ser Thr Tyr Phe Lys Ala Leu Leu
1               5                   10                  15

Gly Pro Arg Asp Thr Arg Val Lys Gly Trp Phe Leu Leu Asp Asn Tyr
                20                  25                  30

Ile Pro Thr Phe Ile Cys Ser Val Ile Tyr Leu Leu Ile Val Trp Leu
            35                  40                  45

Gly Pro Lys Tyr Met Arg Asn Lys Gln Pro Phe Ser Cys Arg Gly Ile
        50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
                100                 105                 110

Leu Trp Trp Tyr Tyr Phe Ser Lys Leu Ile Glu Phe Met Asp Thr Phe
            115                 120                 125

Phe Phe Ile Leu Arg Lys Asn Asn His Gln Ile Thr Val Leu His Val
        130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
                180                 185                 190

Arg Pro Tyr Leu Trp Trp Lys Lys Tyr Ile Thr Gln Gly Gln Leu Leu
            195                 200                 205

Gln Phe Val Leu Thr Ile Ile Gln Thr Ser Cys Gly Val Ile Trp Pro
        210                 215                 220

Cys Thr Phe Pro Leu Gly Trp Leu Tyr Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly

```
                    260                 265                 270
Ser Met Ala Ala Val Asn Gly His Thr Asn Ser Phe Ser Pro Leu Glu
                275                 280                 285

Asn Asn Val Lys Pro Arg Lys Leu Arg Lys Asp
            290                 295

<210> SEQ ID NO 22
<211> LENGTH: 299
<212> TYPE: PRT
<213> ORGANISM: Mus sp.

<400> SEQUENCE: 22

Met Glu His Phe Asp Ala Ser Leu Ser Thr Tyr Phe Lys Ala Phe Leu
1               5                   10                  15

Gly Pro Arg Asp Thr Arg Val Lys Gly Trp Phe Leu Leu Asp Asn Tyr
            20                  25                  30

Ile Pro Thr Phe Val Cys Ser Val Ile Tyr Leu Leu Ile Val Trp Leu
        35                  40                  45

Gly Pro Lys Tyr Met Lys Asn Arg Gln Pro Phe Ser Cys Arg Gly Ile
    50                  55                  60

Leu Gln Leu Tyr Asn Leu Gly Leu Thr Leu Leu Ser Leu Tyr Met Phe
65                  70                  75                  80

Tyr Glu Leu Val Thr Gly Val Trp Glu Gly Lys Tyr Asn Phe Phe Cys
                85                  90                  95

Gln Gly Thr Arg Ser Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His Ala Thr Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Ile Pro Ser Met
            180                 185                 190

Arg Pro Tyr Leu Trp Trp Lys Lys Tyr Ile Thr Gln Gly Gln Leu Val
        195                 200                 205

Gln Phe Val Leu Thr Ile Ile Gln Thr Thr Cys Gly Val Phe Trp Pro
    210                 215                 220

Cys Ser Phe Pro Leu Gly Trp Leu Phe Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Gly His Gln Asn Gly
            260                 265                 270

Ser Val Ala Ala Val Asn Gly His Thr Asn Ser Phe Pro Ser Leu Glu
        275                 280                 285

Asn Ser Val Lys Pro Arg Lys Gln Arg Lys Asp
    290                 295

<210> SEQ ID NO 23
<211> LENGTH: 296
<212> TYPE: PRT
<213> ORGANISM: Homo sapiens
```

<400> SEQUENCE: 23

```
Met Glu His Leu Lys Ala Phe Asp Asp Glu Ile Asn Ala Phe Leu Asp
1               5                   10                  15

Asn Met Phe Gly Pro Arg Asp Ser Arg Val Arg Gly Trp Phe Met Leu
            20                  25                  30

Asp Ser Tyr Leu Pro Thr Phe Phe Leu Thr Val Met Tyr Leu Leu Ser
        35                  40                  45

Ile Trp Leu Gly Asn Lys Tyr Met Lys Asn Arg Pro Ala Leu Ser Leu
50                  55                  60

Arg Gly Ile Leu Thr Leu Tyr Asn Leu Gly Ile Thr Leu Leu Ser Ala
65                  70                  75                  80

Tyr Met Leu Ala Glu Leu Ile Leu Ser Thr Trp Gly Gly Tyr Asn
                85                  90                  95

Leu Gln Cys Gln Asp Leu Thr Ser Ala Gly Glu Ala Asp Ile Arg Val
                100                 105                 110

Ala Lys Val Leu Trp Trp Tyr Tyr Phe Ser Lys Ser Val Glu Phe Leu
            115                 120                 125

Asp Thr Ile Phe Phe Val Leu Arg Lys Lys Thr Ser Gln Ile Thr Phe
130                 135                 140

Leu His Val Tyr His His Ala Ser Met Phe Asn Ile Trp Trp Cys Val
145                 150                 155                 160

Leu Asn Trp Ile Pro Cys Gly Gln Ser Phe Phe Gly Pro Thr Leu Asn
                165                 170                 175

Ser Phe Ile His Ile Leu Met Tyr Ser Tyr Tyr Gly Leu Ser Val Phe
            180                 185                 190

Pro Ser Met His Lys Tyr Leu Trp Trp Lys Lys Tyr Leu Thr Gln Ala
        195                 200                 205

Gln Leu Val Gln Phe Val Leu Thr Ile Thr His Thr Met Ser Ala Val
    210                 215                 220

Val Lys Pro Cys Gly Phe Pro Phe Gly Cys Leu Ile Phe Gln Ser Ser
225                 230                 235                 240

Tyr Met Leu Thr Leu Val Ile Leu Phe Leu Asn Phe Tyr Val Gln Thr
                245                 250                 255

Tyr Arg Lys Lys Pro Met Lys Lys Asp Met Gln Glu Pro Pro Ala Gly
            260                 265                 270

Lys Glu Val Lys Asn Gly Phe Ser Lys Ala Tyr Phe Thr Ala Ala Asn
        275                 280                 285

Gly Val Met Asn Lys Lys Ala Gln
    290                 295
```

<210> SEQ ID NO 24
<211> LENGTH: 292
<212> TYPE: PRT
<213> ORGANISM: Mus sp.

<400> SEQUENCE: 24

```
Met Glu Gln Leu Lys Ala Phe Asp Asn Glu Val Asn Ala Phe Leu Asp
1               5                   10                  15

Asn Met Phe Gly Pro Arg Asp Ser Arg Val Arg Gly Trp Phe Leu Leu
            20                  25                  30

Asp Ser Tyr Leu Pro Thr Phe Ile Leu Thr Ile Thr Tyr Leu Leu Ser
        35                  40                  45

Ile Trp Leu Gly Asn Lys Tyr Met Lys Asn Arg Pro Ala Leu Ser Leu
50                  55                  60
```

```
Arg Gly Ile Leu Thr Leu Tyr Asn Leu Ala Ile Thr Leu Leu Ser Ala
 65                  70                  75                  80

Tyr Met Leu Val Glu Leu Ile Leu Ser Ser Trp Glu Gly Gly Tyr Asn
                 85                  90                  95

Leu Gln Cys Gln Asn Leu Asp Ser Ala Gly Glu Gly Asp Val Arg Val
            100                 105                 110

Ala Lys Val Leu Trp Trp Tyr Tyr Phe Ser Lys Leu Val Glu Phe Leu
            115                 120                 125

Asp Thr Ile Phe Phe Val Leu Arg Lys Lys Thr Asn Gln Ile Thr Phe
        130                 135                 140

Leu His Val Tyr His His Ala Ser Met Phe Asn Ile Trp Trp Cys Val
145                 150                 155                 160

Leu Asn Trp Ile Pro Cys Gly Gln Ser Phe Phe Gly Pro Thr Leu Asn
                165                 170                 175

Ser Phe Ile His Ile Leu Met Tyr Ser Tyr Tyr Gly Leu Ser Val Phe
            180                 185                 190

Pro Ser Met His Lys Tyr Leu Trp Trp Lys Lys Tyr Leu Thr Gln Ala
            195                 200                 205

Gln Leu Val Gln Phe Val Leu Thr Ile Thr His Thr Leu Ser Ala Val
        210                 215                 220

Val Lys Pro Cys Gly Phe Pro Phe Gly Cys Leu Ile Phe Gln Ser Ser
225                 230                 235                 240

Tyr Met Met Thr Leu Val Ile Leu Phe Leu Asn Phe Tyr Ile Gln Thr
                245                 250                 255

Tyr Arg Lys Lys Pro Val Lys Lys Glu Leu Gln Glu Lys Glu Val Lys
            260                 265                 270

Asn Gly Phe Pro Lys Ala His Leu Ile Val Ala Asn Gly Met Thr Asp
            275                 280                 285

Lys Lys Ala Gln
        290

<210> SEQ ID NO 25
<211> LENGTH: 194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tgccttccag gtgcagttcg tactcaccat cacgcacacg ctgagtgccg tggtgaagcc      60
ctgtggcttt cccttcggct ggctcatctt ccagtcttcc tatatgatga cgttagtcat     120
cctgttctta aacttctata ttcaggtaag taagatgtga gtgttcaggg gcaggcaaca     180
tatcagacag ccca                                                       194

<210> SEQ ID NO 26
<211> LENGTH: 17
<212> TYPE: PRT
<213> ORGANISM: Mus sp.

<400> SEQUENCE: 26

Phe Pro Phe Gly Cys Leu Ile Phe Gln Ser Ser Tyr Met Met Thr Leu
  1               5                  10                  15

Val

<210> SEQ ID NO 27
```

```
<211> LENGTH: 51
<212> TYPE: DNA
<213> ORGANISM: Mus sp.

<400> SEQUENCE: 27
gaccagcgtc atcatatagg aagactggaa gatgagacag ccaaagggga a          51

<210> SEQ ID NO 28
<211> LENGTH: 51
<212> TYPE: DNA
<213> ORGANISM: Mus sp.

<400> SEQUENCE: 28
gactaacgtc atcatatagg aagactggaa gatgagccag ccgaagggaa a          51

<210> SEQ ID NO 29
<211> LENGTH: 17
<212> TYPE: PRT
<213> ORGANISM: Mus sp.

<400> SEQUENCE: 29

Phe Pro Phe Gly Trp Leu Ile Phe Gln Ser Ser Tyr Met Met Thr Leu
1               5                   10                  15

Val

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 30
gtcttcctat atgatgacgc ngg                                         23

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtctcccttg atatgatgaa gcagg                                       25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcttcctaa atgatgcagg cagg                                        24
```

DEMETHYLATION TO TREAT EYE DISEASE

CROSS REFERENCE TO RELATED APPLICATIONS

This application claims the priority benefit of U.S. Provisional Application Nos. 62/683,292 and 62/716,554, filed Jun. 11, 2018 and Aug. 9, 2018, respectively, which applications are incorporated herein by reference.

SEQUENCE LISTING

The instant application contains a Sequence Listing which has been submitted electronically in ASCII format and is hereby incorporated by reference in its entirety. Said ASCII copy, created on May 20, 2019, is named 24978-0494_SL.txt and is 17,271 bytes in size.

FIELD OF THE INVENTION

The present invention is directed to the fields of ophthalmology and cell biology. Specifically, the invention regards treatment of age-related macular degeneration (AMD), and other eye diseases.

BACKGROUND

From a population perspective, chronological age is arguably the most important biological trait in predicting age-related disease risks, mental and physical performance, and mortality [1]. The use of chronological age is limited, however, in explaining the large biological variation among individuals of a similar age. Biological age is a concept that attempts to quantify different aging states influenced by lifestyle, genetics, disease, and environment. Environmental and lifestyle choices such as smoking and diet also have clear implications with respect to age-associated diseases [2]. While epidemiological studies have succeeded in providing quantitative assessments of their impact on human longevity, advances in molecular biology now offer the ability to look beyond population questions of mortality, and to hone in on the specific effects of disease and other factors on aging within single organisms.

A quantitative model for aging based on genome-wide DNA methylation patterns by using measurements at 470,000 CpG markers from whole blood samples of a large cohort of human individuals spanning a wide age range has been developed [3]. This method is highly accurate at predicting age, and can also discriminate relevant factors in aging, including gender, genetic variants and disease [3, 4]. The model works in multiple tissues, suggesting the possibility of a common molecular clock, regulated in part by changes in the methylome. In addition, these methylation patterns are strongly correlated with cellular senescence and aging. Several genes were observed to become progressively more methylated with increasing chronological age. ELOVL2 (Elongation Of Very Long Chain Fatty Acids-Like 2), in particular, very reliably shows increased methylation as humans age, as revealed by the aging model [3].

ELOVL2 encodes a transmembrane protein involved in the synthesis of long (C22 and C24) ω3 and ω6 polyunsaturated fatty acids (VLC-PUFA) [5]. Specifically, ELOVL2 is capable of converting docosapentaenoic acid (DPA) (22:5n-3) to 24:5n-3, which is the precursor of 22:6n-3, docosahexaenoic acid (DHA) [6]. DHA is the major polyunsaturated fatty acid (PUFA) in the retina and brain. Its presence in photoreceptors promotes healthy retinal function and protects against damage from bright light and oxidative stress. Low ELOVL2 expression has been linked to low levels of DHA [7], which in turn has been associated with age-related macular degeneration (AMD), among a host of other retinal degenerative diseases [8]. In general, PUFAs are involved in crucial biological functions including energy production, modulation of inflammation, and maintenance of cell membrane integrity. It is therefore possible that ELOVL2 methylation plays a role in the aging process through the regulation of different biological pathways.

AMD is a degenerative disease of the macula, is the leading cause of blindness among the elderly in developed countries. It is a multifactorial disease involving genetic, environmental, and metabolic factors, and there is currently no cure or effective prevention for it. A number of genes have been identified as risk factors, but many are still unknown. As AMD progresses, the center of vision becomes blurred, and eventually blind spots can develop. AMD occurs in two forms, wet AMD and dry AMD. In dry AMD, which affects about 90% of AMD patients, the focal deposition of acellular, polymorphous debris, called drusen, are usually the first observed clinical hallmarks of the disease. ELOVL4, another fatty acid elongase involved in the synthesis of VLC-PUFAs, is implicated in Stargardt macular dystrophy, a juvenile form of macular degeneration causing vision loss [9, 10].

AMD has been associated with oxidative stress in the retina [11]. Oxidative stress can result in inflammation and contribute to the development of macrophage activation [12]. Oxidized phospholipids have been shown to be reliable markers of oxidative stress, and they initiate inflammation by binding to the retinal pigment epithelium (RPE) and macrophages, activating downstream inflammatory cascades [13]. Oxidation-modified proteins and lipids have also been found in drusen and Bruch's membrane [14]. Phosphatidylcholine, a phospholipid highly enriched in the retina, contains the head group phosphocholine. The oxidation epitope of phosphocholine can be recognized by a natural antibody to phosphocholine, TEPC-15 [15], and has been shown to colocalize with drusen in the human AMD eye [16]. HTRA1, one of the main proteins associated with AMD, is also found to colocalize with drusen in the AMD eye [17]. In addition, several components of the complement cascade, including C3 complement fragments, C5 and the membrane attack complex C5b-9 have been found within drusen [18].

New methods of treatment of age-related macular degeneration are needed.

SUMMARY OF THE INVENTION

The disclosure provides methods for treating age-related eye diseases and conditions. In certain embodiments, the methods comprise administering an effective amount of one or more nucleic acid demethylation compounds to a patient in need. The invention provides methods for treating age-related eye diseases.

In embodiments, the invention provides that the age-related eye disease or condition is age-related macular degeneration.

In embodiments, the invention provides that the demethylating compound is selected from a group consisting of 5-azacytidine, decitabine, zebularine, procainamide, procaine, hydralazine, valproic acid and EGCG.

In embodiments, the invention provides that the composition is formulated for ophthalmic administration.

In embodiments, the invention provides that the administration is parenterally into the eye.

In embodiments, the invention provides methods of treating an age-related eye disease or condition comprising increasing expression of ELOVL2 in a patient in need thereof.

In embodiments, the invention provides that expression is increased by demethylation of ELOVL2 promoter.

In embodiments, the invention provides that expression is increased by administering to the patient in need an effective amount of ELOVL2 mRNA using Adeno-associated virus delivery.

In embodiments, the invention provides that an ophthalmic pharmaceutical composition comprising a nucleic acid demethylating compound in an ophthalmically acceptable formulation.

In embodiments, the invention provides that the demethylating compound is selected from a group consisting of 5-azacytidine, decitabine, zebularine, procainamide, procaine, and EGCG.

In other embodiments the methods comprise administering an effective amount of ELOVL2 mRNA to a subject in need using Adeno-associated virus delivery.

BRIEF DESCRIPTION OF THE DRAWINGS

FIG. 1A shows ELOVL2 expression by qPCR in WI-38 cells at PD35, 45, 55. Higher % of input indicates higher DNA methylation. (**$p<0.005$ ANOVA, *$p<0.05$, t-test). FIG. 1B shows methylation level in ELOVL2 promoter region in WI-38 cells by methylated DNA immunoprecipitation followed by qPCR. Primers amplify region containing CpG markers cg16867657, cg24724428, and cg21572722. FIG. 1C shows proliferation of WI-38 knockdown cells and Luciferase knockdown controls as measured by surface area covered over time. FIG. 1D shows percent senescence by beta-galactosidase staining in WI-38 knockdown cells. (n=3, *$p<0.05$, **$p<0.005$, t-test).

FIG. 2A shows ELOVL2 promoter methylation as measured by MeDIP followed by qPCR in untreated control and 5-Aza-dc treated WI-38 cells. FIG. 2B shows ELOVL2 expression by qPCR in untreated control and 5-Aza-dc treated WI-38 cells. FIG. 2C shows percent senescence by beta-galactosidase staining in WI-38 cells treated with 2 µM 5-Aza-dc. (n=3, *$p<0.05$, t-test).

FIG. 3A shows ELOVL2 expression in mouse retina by qPCR in mice of varying age. FIG. 3B shows western blot of ELOVL2 in mouse retinas of varying age; asterisk—non-specific band. FIG. 3C shows ELOVL2 promoter methylation in mouse retinas of varying age. FIG. 3D shows autofluorescence imaging of wild-type mice at 2, 6, 12, and 24 months of age. Representative ERG traces of scotopic responses are shown underneath the images. FIG. 3E shows scotopic response in mice of varying age, shown through ERG b-wave amplitude. (n=4, **$p<0.005$, ANOVA).

FIG. 4A shows CRISPR-Cas9 mediated strategy of changing the substrate specificity of ELOVL2. FIG. 4A discloses SEQ ID NOS 17-20, respectively, in order of appearance. FIG. 4B shows autofluorescence imaging of wild-type and homozygous fate-switch mouse eye fundus. Scotopic ERG responses are shown in traces underneath the images. FIG. 4C shows scotopic b-wave amplitude from ERG in 6-month wild-type and frameshift mutation mice. FIG. 4D shows immunostaining of Htral and T-15 in WT and C217W mouse retinas. Arrows indicate drusen-like aggregates. FIG. 4E shows quantification of drusen-like aggregates positive for HTRA1 and T-15. (n=4, *$p<0.05$, **$p<0.005$, t-test).

FIG. 5A shows ELOVL2 methylation by MeDIP in mouse retinas after intraocular injection with PBS or 5-Aza-dc. FIG. 5B shows ELOVL2 expression by qPCR in mouse retinas after intraocular injection with PBS or 5-Aza-dc. FIG. 5C shows scotopic ERG response in mouse eyes after intraocular injection with PBS or 5-Aza-dc. FIG. 5D shows scotopic b-wave amplitude from ERG. (n=4, *$p<0.05$, t-test).

FIG. 6A shows proliferation of WI-38 cells as measured by surface area covered at population doublings (PD) 35, 45, 55. FIG. 6B shows percent senescence by beta-galactosidase staining in WI-38 cells. FIG. 6C shows representative images of cell morphology and beta-galactosidase staining of WI-38 cells. FIG. 6D shows representative images of cell morphology and beta-galactosidase staining of ELOVL2 knockdown WI38 cells, compared to luciferase knockdown controls. FIG. 6E shows ELOVL2 knockdown efficiency in WI-38 cells by qPCR. (n=3, **$p<0.005$, t-test).

FIG. 7A shows proliferation of IMR-90 cells as measured by surface area covered at population doublings (PD) 35, 45, 55. FIG. 7B shows percent senescence by beta-galactosidase staining in IMR-90 cells. FIG. 7C shows ELOVL2 expression by qPCR in IMR-90 cells. FIG. 7D shows ELOVL2 knockdown efficiency in IMR-90 cells by qPCR. FIG. 7E shows representative images of ELOVL2 knockdown morphology with luciferase knockdown control in IMR90 cells. (n=3, *$p<0.05$, **$p<0.005$, t-test).

FIG. 8A shows autofluorescence images of WT mouse retinas at 2 months, 6 months, 1 year, and 2 years of age. FIG. 8B shows scotopic response of ERG in WT mice at 2 months, 6 months, 1 year, and 2 years of age. FIG. 8C shows oscillatory potentials from ERG in 3-month and 2-year old wild-type mice. FIG. 8D shows 10 Hz flicker response from ERG in 3-month and 2-year old wild-type mice.

FIG. 9A shows a mouse Retina MeDIP of Ames mice. Higher % of input indicates higher DNA methylation. Y=3 months old WT, O=2 years old WT, AY=3 months old Ames, AO=2 years old Ames. FIG. 9B shows an ELOVL2 expression in Ames mice by qPCR. (n=3, *$p<0.05$, **$p<0.005$, t-test).

FIG. 10A shows an ELOVL2 and ELOVL5 amino acid sequence similarity between human and mouse. Red arrowheads denote targeted C217W mutation. FIG. 10A discloses SEQ ID NOS 21-24, respectively, in order of appearance. FIG. 10B shows the target cleavage site for CAS9. FIG. 10C shows an ELOVL2 repair oligo sequence (SEQ ID NO: 25). FIG. 10D shows a protein sequence alignment of WT and C217W. Mutations are highlighted in blue. FIG. 10D discloses SEQ ID NOS 26-29, respectively, in order of appearance. FIG. 10E shows an off-target analysis of ELOVL2 mutant mice. FIG. 10E discloses SEQ ID NOS 30, 31, 30, and 32, respectively, in order of appearance.

FIGS. 11A-11D show an aging characteristics of C217W mouse retinas. FIG. 11A shows an autofluorescence images of WT vs C217W mouse retinas at 4 months, 6 months, 8 months, and 1 year of age. FIG. 11B shows scotopic response of ERG in WT vs. C217W mice at 4 months, 6 months, and 8 months of age. FIG. 11C shows an oscillatory potentials from ERG in wild-type and frameshift mutation mice. FIG. 11D shows a 10 Hz flicker response from ERG in wild-type and frameshift mutation mice.

FIG. 12A shows an immunostaining of Htral, C3, and C5b-9 in WT and C217W mouse retinas. Arrows indicate drusen-like aggregates. FIG. 12B shows a quantification of drusen-like aggregates positive for C3 and C5b-9. FIG. 12C shows an immunostaining of C3 and in WT and C217W mouse retinas. Arrows indicate drusen-like aggregates. FIG. 12D shows a quantification of drusen-like aggregates positive for C3. (n=4, **p<0.005, t-test).

DETAILED DESCRIPTION

Figures 1A, 1B, 1C, 1D:
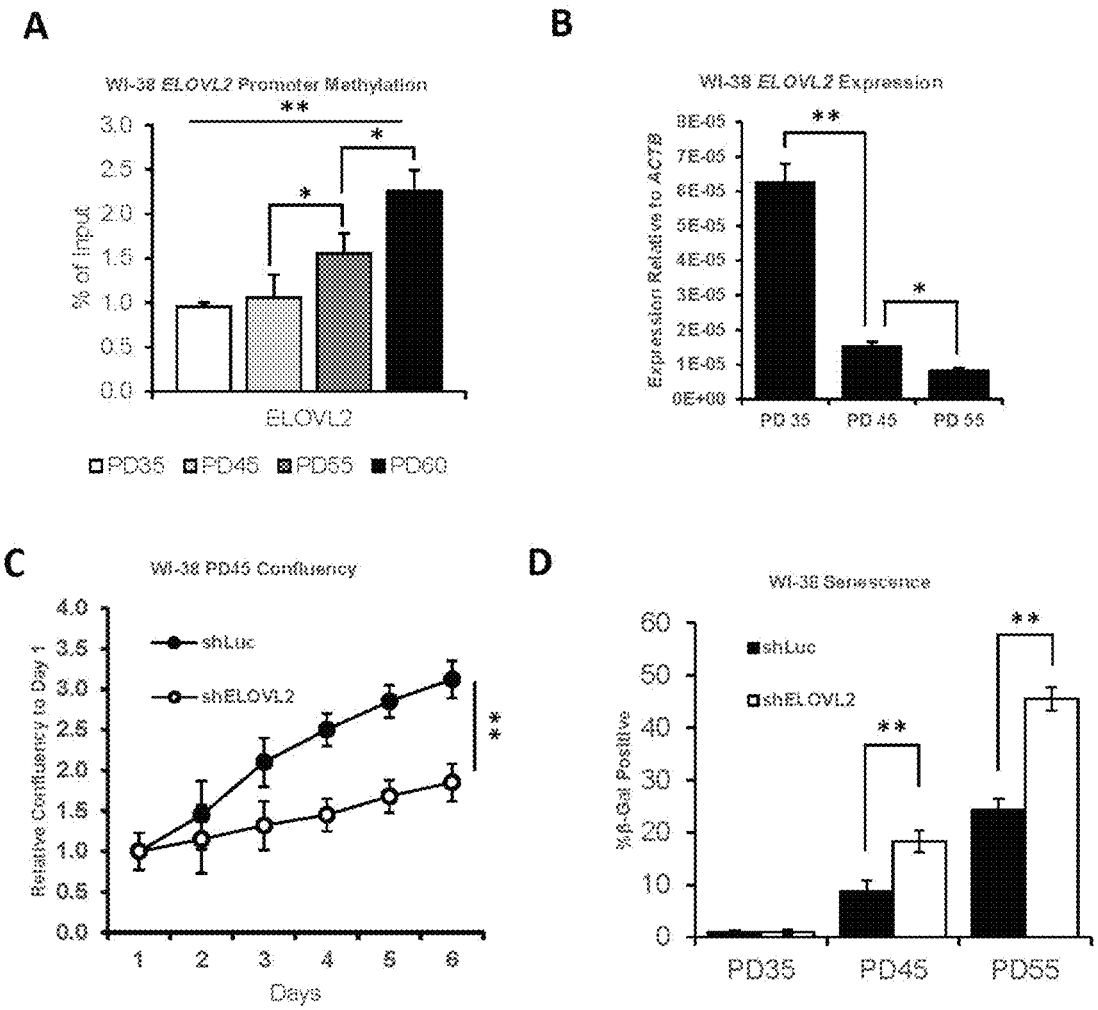
FIGS. 1A-1D show ELOVL2 expression and methylation in WI-38 cells.

All publications, patents, and patent applications mentioned in this specification are herein incorporated by reference to the same extent as if each individual publication, patent, or patent application was specifically and individually indicated to be incorporated by reference.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2n^d$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutical acceptable compositions, wherein the composition comprises demethylation compound(s), and in some embodiments further comprises a pharmaceutically acceptable carrier. In some embodiments, the pharmaceutical composition may be a combination.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of demethylation compound(s) that is sufficient to treat or ameliorate, or in some manner reduce the symptoms associated with age-related eye diseases, such as but not limited to age-related macular degeneration (AMD). When used with reference to a method, the method is sufficiently effective to treat or ameliorate, or in some manner reduce the symptoms associated with age-related eye diseases. For example, an effective amount in reference to age-related eye diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the term "treatment" embraces at least an amelioration of the symptoms associated with age-related eye diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

The term "combination" refers to either a fixed combination in one dosage unit form, or a kit of parts for the combined administration where one or more demethylation compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Macular degeneration is a clinical term that is used to describe a family of diseases that are characterized by a progressive loss of central vision associated with abnormalities of the Bruch's membrane, the choroid, the neural retina and/or the retinal pigment epithelium. In the center of the retina is the macula lutea, which is about ¼ to ½ cm. in diameter. The macula provides detailed vision, particularly in the center (the fovea), because the cones are higher in density. Blood vessels, ganglion cells, inner nuclear layer and cells, and the plexiform layers are all displaced to one side (rather than resting above the ones), thereby allowing light a more direct path to the cones. Under the retina is the choroid, a collection of blood vessels embedded within a fibrous tissue, and the pigmented epithelium (PE), which overlays the choroid layer. The choroidal blood vessels provide nutrition to the retina (particularly its visual cells). The choroid and PE are found at the posterior of the eye.

Age-related macular degeneration (AMD), the most prevalent macular degeneration, is associated with progressive loss of visual acuity in the central portion of the visual field, changes in color vision, and abnormal dark adaptation and sensitivity. Two principal clinical manifestations of AMD have been described as the dry, or atrophic, form, and the wet, or exudative, form. The dry form is associated with atrophic cell death of the central retina or macula, which is required for fine vision used for activities such as reading, driving or recognizing faces. About 10-20% of these dry AMD patients progress to the second form of AMD, known as wet AMD.

Wet (neovascular/exudative) AMD is caused by abnormal growth of blood vessels behind the retina under the macula and vascular leakage, resulting in displacement of the retina, hemorrhage and scar formation. This results in a deterioration of sight over a period of months to years. However, patients can suffer a rapid loss of vision. All wet AMD cases are originated from advanced dry AMD. The wet form accounts for 85% of blindness due to AMD. In wet AMD, as the blood vessels leak fluid and blood, scar tissue is formed that destroys the central retina.

Glaucoma is a leading cause of blindness. While the term "glaucoma" is applied to a large number of different disorders of the eye, common to all types of glaucoma is the phenomenon in which pressure within the eye elevates with resultant destruction of the optic nerve. In most forms of glaucoma the pressure elevation is not sensed by the individual, such as by pain or reduced visual acuity until significant loss of vision has occurred. In the healthy eye, fluid (aqueous humor) passes from the anterior chamber through a filter-like mass of tissue (the trabecular meshwork) and thence to a connected series of veins in the sclera. In the most commonly encountered form of glaucoma (open-angle glaucoma) the pressure elevation results from a blockage of the outflow pathway through the trabecular meshwork. Methods of treating glaucoma have taken two general forms, namely medication and surgery.

Diabetes is the fourth leading cause of death affecting almost 16 million Americans, a third of them undiagnosed, costing over $100 billion per year, 15% of U.S. health-care dollars. Some 800,000 new cases of diabetes develop every year. By the year 2030, the number could reach 50 million here and at least 300 million worldwide. Diabetes mellitus is the leading cause of new blindness among persons 20 to 74 years of age in the United States. Retinopathy begins to develop soon after the diagnosis of insulin-dependent diabetes mellitus (IDDM), and after 15 years, the prevalence is almost 100%. One million people in the U.S. have IDDM or Type I diabetes. In non-insulin-dependent diabetes (NIDDM) or Type II diabetes, currently 15 million, about 21% of the patients have retinopathy at diagnosis, and 60% after 20 years. Type II diabetics have tripled over the last 30 years, and involves half of Americans over the age of 65. Proliferative retinopathy occurs in 10-20% of NIDDM. Brechner R J, et al, JAMA 1993; 270:1714-1718.

Macular degeneration, or age-related macular degeneration (AMD), affects the central part of the retina and is the leading cause of blindness in people over age 65 in the U.S. AMD affects 13 million people and causes impairment in about 1.2 million. About 30% of patients over 75 have AMD, and 23% of the remainder will develop it within five years. The prevalence of AMD increases with age from 16.8% in patients 55-64 to 25.6% in patients 65-74 and up to 42% in patients over 75. There currently is no known cure for dry or atrophic AMD, the form characterized by hard or soft drusen (deposits of cellular debris), changes in the retinal pigment epithelium (RPE), or atrophy of photoreceptors and RPE. This form accounts for approximately 90% of all cases. The remainder of AMD cases have the "wet" form characterized by neovascularization and exudation. Pratt S G, Review of Ophthalmology August 1998:42-50.

The present invention relates to demethylation agents for the treatment of ocular related conditions or diseases, such as age-related macular degeneration (AMD), diabetic retinopathy, ocular angiogenesis (such as ocular neovascularization affecting choroidal, corneal, or retinal tissue), and other ocular conditions involving methylation of genes, such as ELOVL2. Treatment of AMD includes both the dry and wet forms of AMD.

The disclosure provides a method for treating, ameliorating or preventing an age-related eye disease or condition comprising administering an effective amount of at least one demethylation agent to a subject in need of treatment.

In embodiments, the present invention provides that the demethylation agent increases the expression of the elongation of very long chain fatty acids-like 2 gene (ELOVL2) and/or increase the level of ELOVL2 enzyme and /or increase the level of retinal 22:6(n-3) docosahexaenoic (DHA) and 22:5(n-6), docosapentaenoic acid (DPA).

In embodiments, the present invention provides that the demethylation agent is selected from 5-azacytidine, decitabine, zebularine, procainamide, procaine, hydralazine, valproic acid and epigallocatechin gallate (EGCG).

In embodiments, the present invention provides that the demethylating agent is administered to the eye by an intravitreal, subretinal, subconjunctival, subtenon, or posterior juxtascleral route.

In embodiments, the present invention provides that the age-related eye disease is age-related macular degeneration (AMD), diabetic eye disease, glaucoma, low vision or dry eye.

In embodiments, the present invention provides that the demethylating agent is administered as a time-released formulation.

In embodiments, the present invention provides a method for treating, ameliorating or preventing an age-related eye disease or condition comprising increasing ELOVL2 enzyme and/or the level of 22:6(n-3) docosahexaenoic (DHA) and 22:5(n-6) docosapentaenoic acid (DPA) in the eye by administering an effective amount of mRNA encoding ELOVL2 to the eye; wherein the mRNA is delivered using a viral vector.

In embodiments, the present invention provides that the viral vector is selected from an adenoviral vector, adeno-associated virus vector, lentivirus vector, vaccinia virus vector and retroviral vector.

In embodiments, the present invention provides that the mRNA is delivered using a non-viral vector such as a liposome, or micro/nanoparticle.

In embodiments, the present invention provides that the agent is administered to the eye by an intravitreal, subretinal, subconjunctival, subtenon, or posterior juxtascleral route.

In embodiments, the present invention provides that the age-related eye disease is age-related macular degeneration (AMD), diabetic eye disease, glaucoma, low vision or dry eye.

In embodiments, the present invention provides a method for treating, ameliorating or preventing an age-related eye disease and condition comprising increasing ELOVL2 enzyme in the eye and /or the level of 22:6(n-3) docosahexaenoic (DHA) and 22:5(n-6) docosapentaenoic acid (DPA) in the eye by gene therapy using an ELOVL2 expression vector.

In embodiments, the present invention provides that the vector is selected from an adenoviral vector, adeno-associated virus vector, lentivirus vector, vaccinia virus vector and retroviral vector.

In embodiments, the present invention provides that the ELOVL2 expression vector is administered by an intravitreal, subretinal, subconjunctival, subtenon, or posterior juxtascleral route.

In embodiments, the present invention provides that the age-related eye disease is age-related macular degeneration (AMD), diabetic eye disease, glaucoma, low vision or dry eye; and wherein the age-related eye disease is dry AMD.

In embodiments, the present invention provides a method comprising selecting a patient in need of treatment of an age-related eye disease and administering an effective amount of one or more demethylating agents and/or mRNA encoding ELOVL2 and/or an ELOVL2 expression vector to the eye of the patient whereby the age-related disease is treated.

In embodiments, the present invention provides that the patient is selected by determining the methylation of ELOVL2 and/or ELOVL2 expression in the eye of the patient.

In embodiments, the present invention provides that the demethylating agent is decitabine.

In embodiments, the present invention provides that the age-related eye disease is age-related macular degeneration (AMD), diabetic eye disease, glaucoma, low vision or dry eye; and wherein the age-related eye disease is dry AMD.

In embodiments, the present invention provides a method comprising using mRNA encoding ELOVL2 in the treatment of an age-related eye disease, optionally dry AMD.

In embodiments, the present invention provides a method comprising using an ELOVL2 expression vector in the treatment of an age-related eye disease, optionally dry AMD.

In embodiments, the present invention provides a formulation containing a concentration of a demethylating agent listed whereby intravitreal administration 1 uL-100 uL constitutes an effective amount of between 5 ng-500 ng.

In embodiments, the present invention provides a formulation containing a concentration of a demethylating agent listed whereby intravitreal administration 1 ul-100 uL constitutes an effective amount of between 500 ng-1,500 ng.

In embodiments, the present invention provides a formulation containing a concentration of a demethylating agent listed whereby intravitreal administration 1 ul-100 uL constitutes an effective amount of between 1,500 ng-4,500 ng.

In embodiments, the present invention provides that the formulation is substantially aqueous. In embodiments, the present invention provides that the formulation is a substantially anhydrous. In embodiments, the present invention provides that the formulations are immediate release and/or extended release.

In embodiments, the present invention provides that the demethylating agent is decitabine.

In embodiments, the present invention provides a method of making a medicament for administration.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human. In particular embodiments, a subject having AMD is a subject who has been previously diagnosed as having age-related macular degeneration.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

As used herein, and unless otherwise specified, an analog, such as cytidine, referred to herein is intended to encompass the free base of the cytidine analog, or a salt, solvate, hydrate, cocrystal, complex, prodrug, precursor, metabolite, and/or derivative thereof. In certain embodiments, a cytidine analog referred to herein encompasses the free base of the cytidine analog, or a salt, solvate, hydrate, cocrystal or complex thereof. In certain embodiments, a cytidine analog referred to herein encompasses the free base of the cytidine analog, or a pharmaceutically acceptable salt, solvate, or hydrate thereof.

This invention features use of agents to demethylate the promoter of ELOVL2, to induce expression of the gene and improve visual function of a mammal, using certain compounds such as 5-Azacytidine, Decitabine, Zebularine, Procainamide, Procaine, Procaine, Epigallocatechin gallate, Valproic acid, Hydralazine, and similar compounds and derivatives. Collectively these are described herein as a "Demethylation Agent".

In one embodiment, Demethylation Agent is injected intraocularly, for example by subconjuctival, intravitreal, subretinal, or retrobulbar injection. For subconjunctival injection, a concentration in the range of about 1 ng/ml to about 500 µg/ml may be used. For intravitreal injection, a concentration in the range of about 1 µg/0.1 ml to about 1000 µg/0.1 ml may be used; one concentration that may be used is about 50 µg/0.1 ml. For subretinal injection, a concentration in the range of about 1 µg/0.1 ml to about 100 µg/0.1 ml may be used. For retrobulbar injection, a concentration in the range of about 20 µg/ml to about 1000 µg/ml may be used. Demethylation Agent may be administered in an aqueous-based solution, for example, bound to liposomes, or it may be dissolved in an organic solvent. In another alternative embodiment, Demethylation Agent may also be provided in an inert physiologically acceptable carrier such as a microsphere, liposome, capsule or polymeric matrix by injection or by surgical implantation in the eye or on the eye. Aqueous solvents that may be used include, but are not limited to, 0.9% saline and 5% dextrose. Organic solvents that may be used include, but are not limited to, dimethylsulfoxide (DMSO) or an alcohol. An implant may provide a time-release form of Demethylation Agent to achieve a constant dose of drug. A method is also disclosed to reduce the onset or progression of diabetic retinopathy, age-related macular degeneration and/or retinitis pigmentosa, by intraocularly administering a composition containing Demethylation Agent, either alone or with other compounds that are related to Demethylation Agent, as the active agent in a pharmaceutically acceptable formulation and in an effective amount without causing substantial toxicity. The composition may contain Demethylation Agent as the sole active agent, the other agents being those that do not materially affect the basic properties of Demethylation Agent. Alternatively, the composition may contain other active agents, besides Demethylation Agent. The composition may be injected or implanted in the eye. The invention encompasses a method to treat a patient by intraocularly administering a composition containing Demethylation Agent as the active agent in a pharmaceutically acceptable formulation and in an amount effective to treat macular degeneration, retinopathy, or retinitis pigmentosa without substantial ocular toxicity. The composition is injected or implanted in the eye, and may be administered in a time-release formulation. A sustained release formulation, such as a matrix, may be loaded with an amount of Demethylation Agent that may be toxic if released at a non-controlled rate, or a supratherapeutic amount, but which is formulated to release a non-toxic therapeutic amount of Demethylation Agent over a period of time. For example, a matrix may contain from about 1 microgram—to over 10 micrograms. Demethylation Agent and may sustainedly release a non-toxic maintenance dose of Demethylation Agent. Such a matrix may be a diffusible walled reservoir and may be lipid, polyvinyl alcohol, polyvinyl acetate, polycaprolactone, poly(glycolic) acid, and/or poly(lactic)acid.

Demethylation Agent may be injected intraocularly using intravitreal (into the vitreous), subconjuctival (into the subconjuctival), subretinal (under the retina), or retrobulbar (behind the eyeball) injection. For subconjuctival injection, a Demethylation Agent concentration in the range of about 1 ng/ml to about 500 µg/ml may be used. For intravitreal injection, a Demethylation Agent dose in the range of about 10.0 ng/0.1 ml to about 1000 µg/0.1 ml may be used. For retrobulbar injection, a Demethylation Agent dose in the range of about 20 µg/ml to about 1000 µg/ml may be used. For subretinal injection, a Demethylation Agent dose in the range of about 1 µg/0.1 ml to about 100 µg/0.1 ml may be used. However these dosages pertain to immediate release formulations and higher concentrations of Demethylation Agent would be required for more extended release formulations. Demethylation Agent may be administered intraocularly in a composition in which it is the only active agent. Alternatively, Demethylation Agent may be administered intraocularly in a composition with related compounds. Related compounds may include immunosuppressants that include, but are not limited to, tacrolimus, cyclophosphamide, sirolimus, atoposide, thioepa, methotrexate, azathioprine (imuran), interferons, infliximab, etanercept, mycophenolate mofetil, 15-deoxyspergualin, thalidomide, glatiramer, leflunomide, vincristine, cytarabine, etc. In one embodiment, the composition containing Demethylation Agent is administered in an amount or at a dose that does not result in substantial toxicity to the eye. As used herein, a lack of substantial toxicity encompasses both the absence of any manifestations of toxicity, as well as manifestations of toxicity which one skilled in the art would consider not sufficiently detrimental to decrease or cease treatment. The intravenous solution form of Demethylation Agent may be diluted to achieve the indicated concentration using 0.9% NaCl or 5% dextrose, or an organic solvent such as dimethylsulfoxide (DMSO) or alcohol. Intraocular administration may be by any of the routes and formulations previously described. For injection, either a solution, emulsion, suspension, capsular formulation of microspheres or liposomes, etc. may be used. Demethylation Agent may be administered surgically as an ocular implant. As one example, a reservoir container having a diffusible wall of polyvinyl alcohol or polyvinyl acetate and containing milligram quantities of Demethylation Agent may be implanted in or on the sclera. As another example, Demethylation Agent in milligram quantities may be incorporated into a polymeric matrix having dimensions of about 2 mm by 4 mm, and made of a polymer such as polycaprolactone, poly(glycolic) acid, poly (lactic) acid, or a polyanhydride, or a lipid such as sebacic acid, and may be implanted on the sclera or in the eye. This is usually accomplished with the patient receiving either a topical or local anesthetic and using a small (3-4 mm incision) made behind the cornea. The matrix, containing Demethylation Agent, is then inserted through the incision and sutured to the sclera using 9-0 nylon. Demethylation Agent may be contained within an inert matrix for injection into the eye. As one example of an inert matrix, liposomes may be prepared from dipalmitoyl phosphatidylcholine (DPPC), such as egg phosphatidylcholine (PC), a lipid having a low heat transition. Liposomes are made using standard procedures as known to one skilled in the art. Demethylation Agent, in amounts ranging from nanogram to microgram to milligram quantities, is added to a solution of egg PC, and the lipophilic drug binds to the liposome. A time-release drug delivery system may be implanted intraocularly to result in sustained release of the active agent over a period of time. The implantable structure may be in the form of a capsule of any of the polymers previously disclosed (e.g., polycaprolactone, poly(glycolic)acid, poly (lactic)acid, polyanhydride) or lipids that may be formulation as microspheres. As an illustrative example, Demethylation Agent may be mixed with polyvinyl alcohol (PVA), the mixture then dried and coated with ethylene vinyl acetate, then cooled again with PVA. In a formulation for intraocular injection, the liposome capsule degrades due to cellular digestion and can be a slow release drug delivery system, allowing the patient a constant exposure to the drug over time. In a time-release formulation, the microsphere, capsule, liposome, etc. may contain a concentration of Demethylation Agent that could be toxic if it were administered as a bolus dose. The time-release administration, however, is formulated so that the concentration released over any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). Depending upon the amount of Demethylation Agent provided in the formulation, a patient could be dosed over a period of years from a single implant or injection. As illustrative but non-limiting examples, a capsule can be loaded with 1-2 mg of Demethylation Agent; if the capsule is formulated to release a few micrograms of drug per day, the patient could be dosed for about 1000 days, or almost three years. As another example, If the capsule is loaded with 5 mg of drug, the patient could be dosed for about fifteen years. Such a formulation provides benefits which include accurate dosing with heightened patient convenience, because intervention is required in some cases only once or twice a decade or even less frequently. The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety. Demethylation Agent, either alone or in combination with other agents, may be administered intraocularly and without substantial toxicity, to treat retinopathy such as occurs in diabetic patients, macular degeneration, and retinitis pigmentosa, using the methods and formulations previously described.

Provided herein are methods for treating an eye disease, including AMD, using a cytidine analog of a salt, solvate, hydrate, precursor, and/or derivative thereof. Certain of the methods provided herein comprise treating an eye disease using a combination of two or more active agents, including 5-azacytidine.

Nucleoside analogs have been tested clinically for the treatment of certain cancers, but not for eye diseases. The nucleoside analogs 5-azacytidine (also known as 4-amino-1β-3-D-ribofuranosyl-1,3,5-triazin-2(1H)-one; National Service Center designation NSC-102816; CAS Registry Number 320-67-2; azacitidine; Aza and AZA; and currently marketed as VIDAZA®) and 2'-deoxy-5-azacytidine (also known as 5-aza-2'-deoxycytidine, decitabine, Dae, and DAC, and currently marketed as DACOGEN®) are DNA methyltransferase (DNMT) inhibitors that have been approved by the U.S. Food and Drug Administration for the treatment of myelodysplastic syndromes (MDS). Azacitidine and decitabine are cytidine analogs; a structural difference between these cytidine analogs and their related natural nucleosides is the presence of a nitrogen at position 5 of the cytosine ring in place of a carbon. Azacitidine may be defined as having a molecular formula of $C_8H_{12}N_4O_5$, a molecular weight of 244.21 grams per mole, and a structure as shown below. Decitabine may be defined as having a molecular formula of $C_8H_{12}N_4O_4$, and a molecular weight of 228.21 grams per mole.

In one embodiment, the methods provided herein comprise administration or co-administration of one or more cytidine analogs. In certain embodiments, the cytidine analog is 5-azacytidine (azacitidine). In certain embodiments, the cytidine analog is 5-aza-2'-deoxycytidine (decitabine). In certain embodiments, the cytidine analog is 5-azacytidine (azacitidine) or 5-aza-2'-deoxycytidine (decitabine). In certain embodiments, the cytidine analog is, for example: 1-β-3-D-arabinofuranosylcytosine (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); N4-pentyloxy-carbonyl-5'-deoxy-5-fluorocytidine (Capecitabine); N4-octadecyl-cytarabine; or elaidic acid cytarabine. In certain embodiments, the cytidine analogs provided herein include any compound which is structurally related to cytidine or deoxycytidine and functionally mimics and/or antagonizes the action of cytidine or deoxycytidine.

Certain embodiments herein provide salts, cocrystals, solvates (e.g., hydrates), complexes, prodrugs, precursors, metabolites, and/or other derivatives of the cytidine analogs provided herein. For example, particular embodiments provide salts, cocrystals, solvates (e.g., hydrates), complexes, precursors, metabolites, and/or other derivatives of 5-azacytidine. Certain embodiments herein provide salts, cocrystals, and/or solvates (e.g., hydrates) of the cytidine analogs provided herein. Certain embodiments herein provide salts and/or solvates (e.g., hydrates) of the cytidine analogs provided herein. Certain embodiments provide cytidine analogs that are not salts, cocrystals, solvates (e.g., hydrates), or complexes of the cytidine analogs provided herein. For example, particular embodiments provide 5-azacytidine in a non-ionized, non-solvated (e.g., anhydrous), non-complexed form. Certain embodiments herein provide a mixture of two or more cytidine analogs provided herein. Cytidine analogs provided herein may be prepared using synthetic methods and procedures referenced herein or otherwise available in the literature. For example, particular methods for synthesizing 5-azacytidine are disclosed, e.g., in U.S. Pat. No. 7,038,038 and references discussed therein, each of which is incorporated herein by reference. Other cytidine analogs provided herein may be prepared, e.g., using procedures known in the art, or may be purchased from a commercial source. In one embodiment, the compound used in the methods provided herein is a free base, or a pharmaceutically acceptable salt or solvate thereof. In one embodiment, the free base or the pharmaceutically acceptable salt or solvate is a solid. In another embodiment, the free base or the pharmaceutically acceptable salt or solvate is a solid in an amorphous form. In yet another embodiment, the free base or the pharmaceutically acceptable salt or solvate is a solid in a crystalline form. For example, particular embodiments provide 5-azacytidine in solid forms, which can be prepared, for example, according to the methods described in U.S. Pat. Nos. 6,943,249, 6,887,855 and 7,078,518, and U.S. Patent Application Publication Nos. 2005/027675 2006/247189, and WO2010/093435, each of which is incorporated by reference herein in their entireties. In other embodiments, 5-azacytidine in solid forms can be prepared using other methods known in the art.

In one embodiment, the compound used in the methods provided herein is a pharmaceutically acceptable salt of the cytidine analog, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

Pharmaceutical Compositions: In one embodiment, provided herein are pharmaceutical compositions, which comprise one or more cytidine analogs, or a pharmaceutically acceptable salt or solvate thereof, as an active ingredient, in combination with one or more pharmaceutically acceptable carrier. In one embodiment, the pharmaceutical composition comprises at least one non-release controlling excipient or carrier. In one embodiment, the pharmaceutical composition comprises at least one release controlling and at least one non-release controlling excipients or carriers.

In certain embodiments, the cytidine analog used in the pharmaceutical compositions provided herein is in a solid form. Suitable solid forms include, but are not limited to, solid forms comprising the free base of the cytidine analog, and solid forms comprising salts of the cytidine analog. In certain embodiments, solid forms provided herein include polymorphs, solvates (including hydrates), and co-crystals comprising the cytidine analog and/or salts thereof. In certain embodiments, the solid form is a crystal form of the cytidine analog, or a pharmaceutically acceptable salt or solvate thereof.

In one embodiment, the pharmaceutical compositions provided herein may be formulated in various dosage forms for optic, intra-vitreal, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art {see, e.g., Remington, The Science and Practice of Pharmacy, 21st Edition; Lippincott Williams & Wilkins: Philadelphia, Pa., 2005; Modified-Release Drug Delivery Technology, Rathbone et al, eds., Drugs and the Pharmaceutical Science, Marcel Dekker, Inc.: New York, N.Y., 2003; Vol. 126). In one embodiment, the pharmaceutical compositions are provided in a dosage form for intra-vitreal administration. In another embodiment, the pharmaceutical compositions are provided in a dosage form for parenteral administration. In yet another embodiment, the pharmaceutical compositions are provided in a dosage form for topical administration.

In one embodiment, the pharmaceutical compositions provided herein may be administered topically to the eye, or intra-vitreally in the forms of inserts, injections, implants, pastes, powders, dressings, creams, plasters, ointments, solutions, emulsions, suspensions, gels, foams, or sprays. These dosage forms can be manufactured using conventional processes as described in, e.g., Remington, The Science and Practice of Pharmacy, supra. The pharmaceutical compositions provided herein for topical administration may be formulated to be immediate release or modified release, including delayed-, sustained-, pulsed-, controlled-, targeted, and programmed release.

Decitabine is currently being developed as a pharmaceutical for the treatment of chronic myelogenous leukemia (CML), myelodysplastic syndrome (MDS), non-small cell lung (NSCL) cancer, sickle-cell anaemia, and acute myelogenous leukemia (AML).

Decitabine may include a formulation comprising: (a) a compound of the formula shown in Figure imgf000003_0001 of WO2013033176, or a pharmaceutically-acceptable salt thereof; dissolved in (b) a substantially anhydrous solvent comprising about 45% to about 85% propylene glycol; about 5% to about 45% glycerin; and 0% to about 30% ethanol. In some embodiments, said solvent comprises about 65% to about 70% propylene glycol; about 25% to about 30% glycerin, and 0% to about 10% ethanol.

The invention provides a composition comprising a Demethylation Agent, and a pharmaceutically acceptable excipient or carrier. The term "pharmaceutically acceptable excipient or carrier" refers to a medium that is used to prepare a desired dosage form of a compound. A pharmaceutically acceptable excipient or carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof. In one embodiment, the pharmaceutically acceptable excipient is not deleterious to a mammal (e.g., human patient) if administered to the eye (e.g., by intraocular injection). For intraocular administration, for example and not limitation, the therapeutic agent can be administered in a Balanced Salt Solution (BSS) or Balanced Salt Solution Plus (BSS Plus) (Alcon Laboratories, Fort Worth, Tex., USA). In a related aspect, the invention provides a sterile container, e.g. vial, containing a therapeutically acceptable Demethylation Agent, optionally a lyophilized preparation.

Another embodiment of the present invention relates to the administration of nucleic acid constructs that are capable of effecting methylation inhibition by gene therapy.

WO 2001/58494 is directed to treating or preventing an ocular disease, such as age-related macular degeneration, by contacting an ocular cell with an expression vector comprising a nucleic acid sequence encoding an inhibitor of angiogenesis and a neurotrophic agent. In specific embodiments, the inhibitor of angiogenesis and the neurotrophic agent are one and the same, such as pigment epithelium-derived factor (PEDF). WO 2002/13812 regards the use of an insulin-sensitizing agent, preferably peroxisome proliferator-activated receptor-γ (PPAR γ) agonists, for the treatment of an inflammatory disease, such as an ophthalmic disease. WO 200/52479 addresses diagnosing, treating, and preventing drusen-associated disorders (any disorder which involves drusen formation), including AMD. In specific embodiments, there are methods related to providing an effective amount of an agent that inhibits immune cell proliferation or differentiation, such as antagonists of TNF-alpha.

In one aspect, the invention provides methods of treating an individual with AMD (e.g., an individual in whom a polymorphism or haplotype indicative of elevated risk of developing symptomatic AMD is detected) or other disease involving a variant ELOVL2 methylation gene. In one embodiment, the method includes administering to the patient an agent that decreases the amount of a variant ELOVL2 methylation or expression of a gene encoding ELOVL2 methylation in an amount effective to reduce a symptom of the disease in the patient. In a related embodiment a therapeutic amount of an inhibitor (e.g., inactivator) of the variant ELOVL2 methylation polypeptide in the individual is administered.

In one embodiment an inhibitory nucleic acid (e.g., an RNA complementary to at least a portion of the nucleotide sequence of the variant ELOVL2 methylation polypeptide) in the individual is administered. In one embodiment, purified anti-sense RNA complementary to RNA encoding a variant ELOVL2 methylation polypeptide is administered.

In another embodiment a therapeutic amount of an anti-ELOVL-2 methylation antibody sufficient to partially inactivate the variant ELOVL2 methylation polypeptide in the individual is administered.

In one aspect, the invention provides gene therapy vectors comprising nucleic acid encoding the ELOVL2 methylation polypeptide. The vector may include a promoter that drives expression of the ELOVL2 methylation gene in multiple cell types. Alternatively, the vector may include a promoter that drives expression of the ELOVL2 methylation gene only in specific cell types, for example, in cells of the retina. In an aspect, pharmaceutical compositions are provided containing a gene therapy vector encoding a ELOVL2 methylation protein and a pharmaceutically acceptable excipient, where the composition is free of pathogens and suitable for administration to a human patient. In one embodiment the encoded ELOVL2 methylation polypeptide is a protective variant.

In one aspect, the invention provides a composition containing recombinant or purified ELOVL2 methylation polypeptide, where the polypeptide is a protective variant.

In a related aspect, the invention provides a pharmaceutical composition containing recombinant or purified ELOVL2 methylation polypeptide and a pharmaceutically acceptable excipient, where the composition is free of pathogens and suitable for administration to a human patient. In one embodiment the encoded ELOVL2 methylation polypeptide has the wild-type sequence. In one embodiment the encoded ELOVL2 methylation polypeptide is a protective variant.

In one aspect, the invention provides antibodies that specifically interact with a variant ELOVL2 methylation polypeptide but not with a wild-type ELOVL2 methylation polypeptide. These antibodies may be polyclonal or monoclonal and may be obtained by subtractive techniques. These antibodies may be sufficient to inactivate a variant ELOVL2 methylation polypeptide. In a related aspect, the invention provides pharmaceutical compositions containing an anti-ELOVL2 methylation antibody and a pharmaceutically acceptable excipient, where the composition is free of pathogens and suitable for administration to a human patient.

In one aspect, the invention provides methods for identifying variant ELOVL2 methylation proteins associated with increased or reduced risk of developing AMD. In one embodiment, the invention provides a method of identifying a protective ELOVL2 methylation protein by (a) identifying an individual as having a protective haplotype and (b) determining the amino acid sequence(s) of ELOVL2 methylation encoded in the genome of the individual, where a protective ELOVL2 methylation protein is encoded by an allele having a protective haplotype. In one embodiment, the invention provides a method of identifying a neutral ELOVL2 methylation protein by (a) identifying an individual as having a neutral haplotype and (b) determining the amino acid sequence(s) of ELOVL2 methylation encoded in the genome of the individual, where a neutral ELOVL2 methylation protein is encoded by an allele having a neutral haplotype. In a related embodiment, the invention provides a method of identifying a variant form of ELOVL2 methylation associated with decreased risk of developing AMD comprising (a) identifying an individual as having a haplotype or diplotype associated with a decreased risk of developing AMD; (b) obtaining genomic DNA or RNA from the individual; and (c) determining the amino acid sequence(s) of the ELOVL2 methylation encoded in the individual's genome, where a protective ELOVL2 methylation protein is encoded by an allele having a haplotype associated with a decreased risk of developing AMD. In an embodiment, the protective or neutral ELOVL2 methylation proteins do not have the amino acid sequence of the wild-type ELOVL2 methylation polypeptide.

As will be understood by those of skill in the art, gene therapy vectors contain the necessary elements for the transcription and translation of the inserted coding sequence (and may include, for example, a promoter, an enhancer, other regulatory elements). Promoters can be constitutive or inducible. Promoters can be selected to target preferential gene expression in a target tissue, such as the RPE (for recent reviews see Sutanto et al., 2005, "Development and evaluation of the specificity of a cathepsin D proximal promoter in the eye" Curr Eye Res. 30:53-61; Zhang et al., 2004, "Concurrent enhancement of transcriptional activity and specificity of a retinal pigment epithelial cell-preferential promoter" Mol Vis. 10:208-14; Esumi et al., 2004, "Analysis of the VMD2 promoter and implication of E-box binding factors in its regulation" J Biol Chem 279:19064-73; Camacho-Hubner et al., 2000, "The Fugu rubripes tyrosinase gene promoter targets transgene expression to pigment cells in the mouse" Genesis. 28:99-105; and references therein).

Suitable viral vectors include DNA virus vectors (such as adenoviral vectors, adeno-associated virus vectors, lentivirus vectors, and vaccinia virus vectors), and RNA virus vectors (such as retroviral vectors). In one embodiment, an adeno-associated viral (AAV) vector is used. For recent reviews see Auricchio et al., 2005, "Adeno-associated viral vectors for retinal gene transfer and treatment of retinal diseases" Curr Gene Ther. 5:339-48; Martin et al., 2004, Gene therapy for optic nerve disease, Eye 18:1049-55; Ali, 2004, "Prospects for gene therapy" Novartis Found Symp. 255:165-72; Hennig et al., 2004, "AAV-mediated intravitreal gene therapy reduces lysosomal storage in the retinal pigmented epithelium and improves retinal function in adult MPS VII mice" Mol Ther. 10:106-16; Smith et al., 2003, "AAV-Mediated gene transfer slows photoreceptor loss in the RCS rat model of retinitis pigmentosa" Mol Ther. 8:188-95; Broderick et al., 2005, "Local administration of an adeno-associated viral vector expressing IL-10 reduces monocyte infiltration and subsequent photoreceptor damage during experimental autoimmune uveitis" Mol Ther. 12:369-73; Cheng et al., 2005, "Efficient gene transfer to retinal pigment epithelium cells with long-term expression. Retina 25:193-201; Rex et al., "Adenovirus-mediated delivery of catalase to retinal pigment epithelial cells protects neighboring photoreceptors from photo-oxidative stress. Hum Gene Ther. 15:960-7; and references cited therein).

Gene therapy vectors must be produced in compliance with the Good Manufacturing Practice (GMP) requirements rendering the product suitable for administration to patients. The present invention provides gene therapy vectors suitable for administration to patients including gene therapy vectors that are produced and tested in compliance with the GMP requirements. Gene therapy vectors subject to FDA approval must be tested for potency and identity, be sterile, be free of extraneous material, and all ingredients in a product (i.e., preservatives, diluents, adjuvants, and the like) must meet standards of purity, quality, and not be deleterious to the patient. For example, the nucleic acid preparation is demonstrated to be mycoplasma-free. See, e.g, Islam et al., 1997, An academic centre for gene therapy research and clinical grade manufacturing capability, Ann Med 29, 579-583.

Methods for administering gene therapy vectors are known. In one embodiment, ELOVL2 expression vectors are introduced systemically (e.g., intravenously or by infusion). In one embodiment, ELOVL2 expression vectors are introduced locally (i.e., directly to a particular tissue or organ, e.g., eye. In one preferred embodiment, ELOVL2 expression vectors are introduced directly into the eye (e.g., by ocular injection). For recent reviews see, e.g., Dinculescu et al., 2005, "Adeno-associated virus-vectored gene therapy for retinal disease" Hum Gene Ther. 16:649-63; Rex et al., 2004, "Adenovirus-mediated delivery of catalase to retinal pigment epithelial cells protects neighboring photoreceptors from photo-oxidative stress" Hum Gene Ther. 15:960-7; Bennett, 2004, "Gene therapy for Leber congenital amaurosis" Novartis Found Symp. 255:195-202; Hauswirth et al., "Range of retinal diseases potentially treatable by AAV-vectored gene therapy" Novartis Found Symp. 255:179-188, and references cited therein).

Thus in one aspect, the invention provides a preparation comprising a gene therapy vector encoding a ELOVL2 protein or ELOVL2 polypeptide, optionally a viral vector, where the gene therapy vector is suitable for administration to a human subject and in an excipient suitable for administration to a human subject (e.g., produced using GLP techniques). Optionally the gene therapy vector comprising a promoter that is expressed preferentially or specifically in retinal pigmented epithelium cells.

Methods for the prevention and treatment of orbital disorders associated with the aging eye in mammals can include the application of a topical composition comprising a permeation enhancing amount of one or more penetration enhancers, and one or more bio-affecting agents which penetrate into the underlying tissues and into the vascular network of the orbit. It is an object of this method to thereby prevent and treat eye diseases like and macular degeneration, but also cataract formation, glaucoma, and diabetic retinopathy.

Delivery of medicament to the eye can be facilitated by a penetration enhancer or permeation enhancer to increase the permeability of the skin to a pharmacologically active agent to increase the rate at which the drug diffuses through the skin and enters the tissues and bloodstream. A chemical skin penetration enhancer increases skin permeability by reversibly altering the physiochemical nature of the stratum corneum to reduce its diffusional resistance.

Many chemical compounds are known to be skin penetration enhancers. Most of the compounds are generally recognized as safe (GRAS) ingredients that would often be considered inert by a formulator. Osborne D W, Henke J J, Pharmaceutical Technology, November 1997, pp 58-86. The compounds cited in the article are incorporated by reference. Examples of penetration enhancers include: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof.

A number of patents disclose the use of penetration enhancers to deliver medications transdermally. U.S. Pat. No. 5,837,289, discloses the use of at least two separate penetration enhancers in a cream to deliver an extensive list of medications. U.S. Pat. No. 5,238,933, discloses a skin permeation enhancer composition comprising a lower aliphatic ester of a lower aliphatic carboxyl acid in combination with a lower alkanol to administer an active agent. U.S. Pat. No. 5,229,130, discloses a vegetable oil-based skin permeation enhancer to deliver active agents through the skin. U.S. Pat. No. 4,933,184, discloses a transdermal composition that uses methanol either sequentially or simultaneously to deliver drugs. U.S. Pat. No. 4,342,784, discloses a method of topically administering a gel with DMSO and carboxy polymethylene resin with a neutralizing agent to enable the skin salt to break down the gel to release the DMSO. U.S. Pat. No. 5,482,965, discloses a transdermal composition containing a dioxane. U.S. Pat. Nos. 5,620,980, 5,807,957, discloses the use of a dioxolane and urethane to treat hair loss.

In one aspect, transconjunctival penetration of Demethylation Agents and therapeutic, pharmaceutical, biochemical and biological agents or compounds can be facilitated by enhancers that can be used to further expedite the entry of these agents into the anterior chamber, trabecular meshwork, ciliary body, choroid and retina. Penetration enhancers not only penetrate a membrane efficiently, but these enhancers also enable other bioactive agents to cross a particular membrane more efficiently. Penetration enhancers produce their effect by various modalities such as disrupting the cellular layers of the conjunctival sac surface interacting with intracellular proteins and lipids, or improving partitioning of bioactive agents as they come into contact with the mucosal membranes.

With these enhancers, macromolecules up to 10 kDa are able to pass through the conjunctival sac layers of the eyes reaching the site of glaucoma where the blood vessels and retina are undergoing pathological changes. These enhancers should be non-toxic, pharmacologically inert, non-allergic substances. In general these enhancers may include anionic surfactants, ureas, fatty acids, fatty alcohols, terpenes, cationic surfactants, nonionic surfactants, zwitterionic surfactants, polyols, amides, lactam, acetone, alcohols, and sugars. In one aspect, the 10 penetration enhancer includes dialkyl sulfoxides such as dimethyl sulfoxide (DMSO), decyl methyl sulfoxide, dodecyl dimethyl phosphine oxide, octyl methyl sulfoxide, nonyl methyl sulfoxide, undecyl methyl sulfoxide, sodium dodecyl sulfate and phenyl piperazine, or any combination thereof. In another aspect, the penetration enhancer may include lauryl alcohol, diisopropyl sebacate, oleyl alcohol, diethyl sebacate dioctyl sebacate, dioctyl azelate, hexyl laurate, ethyl caprate, butyl stearate, dibutyl sebacate, dioctyl adipate, propylene glycol dipelargonate, ethyl laurate, butyl laurate, ethyl myristate, butyl myristate, isopropyl palmitate, isopropyl isostearate, 2-ethylhexyl pelargonate, butyl benzoate, benzyl benzoate, benzyl salicylate, dibutyl phthalate, or any combination thereof. In one aspect, the skin permeability enhancer is at least greater than 1% weight per volume, weight per weight, or mole percent.

In another aspect, the mucosal membrane permeability enhancer may be at least greater than 1.5%, 2.0%, 2.5%, 3.0%. 3.5%. 4.0%. 4.5% up to 50% weight per volume, weight per weight, or mole percent. In one aspect, the mucosal membrane permeability enhancer is dimethyl sulfoxide. In this aspect, the amount of dimethyl sulfoxide may range from 2% to 10%. 2% to 9.5%. 3% to 8%. 3% to 7% or 4% to 6% weight per volume, weight per weight, by mole percent, or any effective therapeutic amount.

The therapeutic preparation may also contain non-toxic emulsifying, preserving, wetting agents, bodying agents, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic. Furthermore, appropriate ophthalmic vehicles can be used as carrier media for the current purpose including conventional phosphate buffer vehicle systems, isotonic boric acid vehicles, isotonic sodium chloride vehicles, isotonic sodium borate vehicles and the like.

The Demethylation Agent therapeutic agents preparation may also contain surfactants such as polysorbate surfactants, polyoxyethylene surfactants (BASF Cremaphor), phosphonates, saponins and polyethoxylated castor oils and polyethoxylated castor oils which are commercially available.

The pharmaceutical preparation may too contain wetting agents that are already in used in ophthalmic solutions such as arboxymethylcellulose, hydroxypropyl methylcellulose, glycerin, mannitol, polyvinyl alcohol or hydroxyethylcellulose and the diluting agent may be water, distilled water, sterile water, or artificial tears. The wetting agent is present in an amount of about 0.001% to about 10%.

The ophthalmic formulation of this invention may include acids and bases to adjust the pH; tonicity imparting agents such as sorbitol, glycerin and dextrose; other viscosity imparting agents such as sodium carboxymethylcellulose, polyvinylpyrrdidone, polyvinyl alcohol and other gums; suitable absorption enhancers, such as surfactants, bile acids; stabilizing agents such as antioxidants, like bisulfites and ascorbates; metal chelating agents, such as sodium EDTA; and drug solubility enhancers, such as polyethylene glycols. These additional ingredients help make commercial solutions with stability so that they need not be compounded as needed.

Ophthalmic medications compositions will be formulated so as to be compatible with the eye and/or contact lenses. The eye drop preparation should be isotonic with blood. As will be the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 210-320 millimoles per kilogram (mOsm/kg).

EXAMPLES

WI-38 and IMR-90 cell lines have been previously described as extensively used models to study cellular aging.

Figures 6A, 6B, 6C, 6D, 6E:
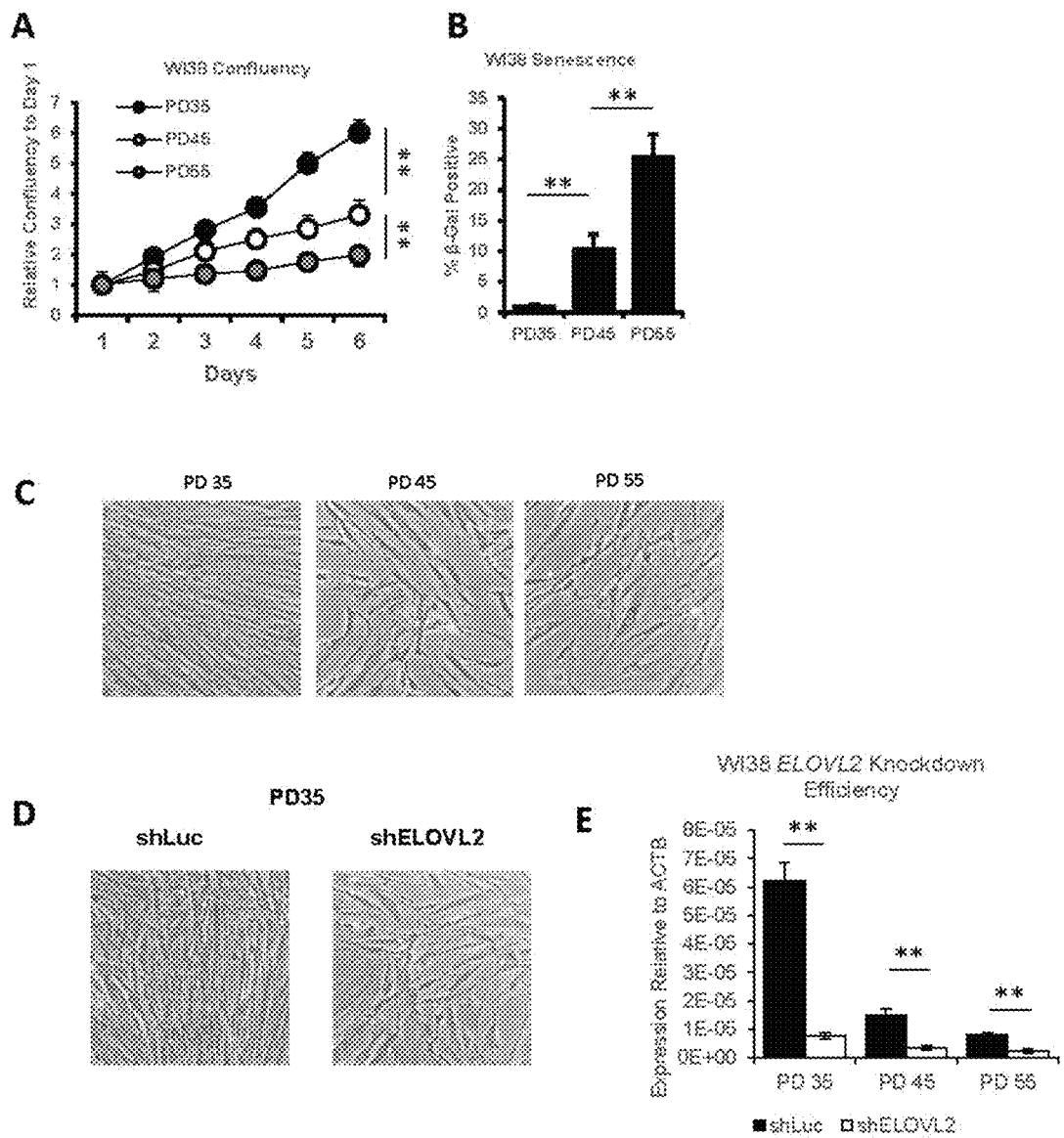
FIGS. 6A-6E show aging characteristics of WI-38 cells.
Figures 7A, 7B, 7C, 7D, 7E:
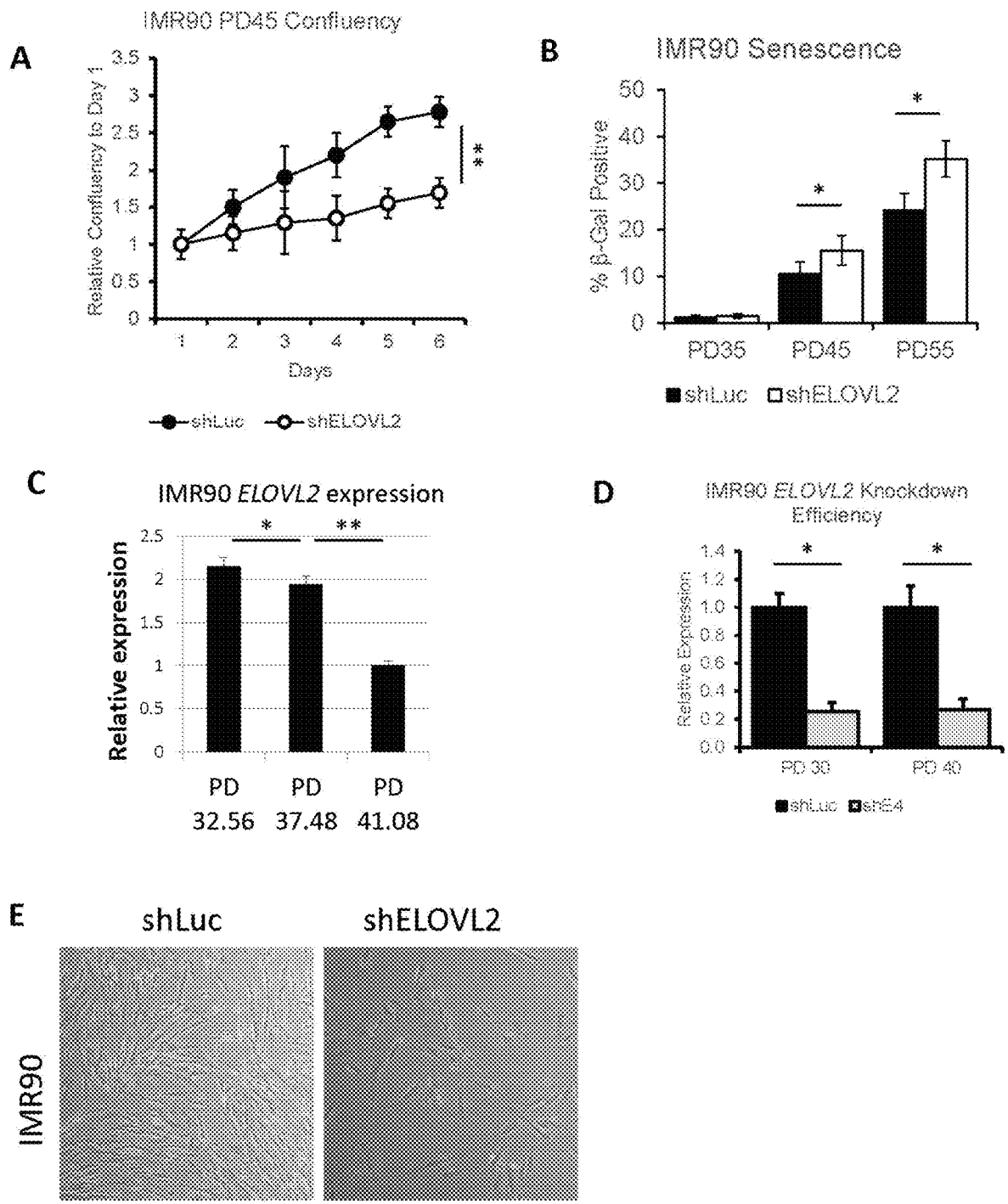
FIGS. 7A-7E show aging characteristics of IMR-90 cells.

It has been shown that both cell lines show significant changes in phenotype over time and population doubling (PD) number [19, 20]. Their growth rate, measured as confluency by imaging software, markedly decreases from lower PD to higher PD (FIGS. 6A and 7A). The percentage of senescence-positive cells, as measured by senescence-associated beta-galactosidase staining (SA-β-Gal) increases as PD increases (FIG. 6B and FIG. 7B), and their morphology changes from a more elongated shape to a broader, flatter shape (FIG. 6C).

Studies on the methylation profiles of human aging indicated that methylation of the promoter region of ELOVL2 is by far the most significantly correlated with age [3]. To investigate the changes in level of ELOVL2 promoter methylation in aging WI38 and IMR90 cells, Methylated DNA Immunoprecipitation (MeDIP) was used. Primers encompassing the specific CpGs described in Table 1 were designed. Using this approach, it was found that promoter methylation rises with increasing cell population doubling (FIG. 1A). As it has been previously shown that methylation of the promoter region is inhibitory for transcription [21], whether the expression level of ELOVL2 inversely correlates with ELOVL2 promoter methylation was investigated. Using qRT-PCR, it was found that the expression level of the gene decreases with increasing PD number (FIG. 1B and FIG. 7C), leading to the conclusion that ELOVL2 expression is downregulated in aging cells, with accompanying increases in ELOVL2 promoter methylation and percentage of senescent cells in culture.

Whether modulating the expression of ELOVL2 could influence cellular aging was investigated. First, using lentiviral shRNA, ELOVL2 expression in WI-38 and IMR-90 cells was knocked down (FIG. 6E and FIG. 8D) and a significant decrease in proliferation rate was observed (FIG. 1C), as well as an increased number of senescent cells in culture as detected by SA-β-Gal staining (FIG. 1D), and morphological changes consistent with high PD cells (FIG. 6D). All the observations together indicated an increase in apparent fibroblast age.

Figures 2A, 2B, 2C:
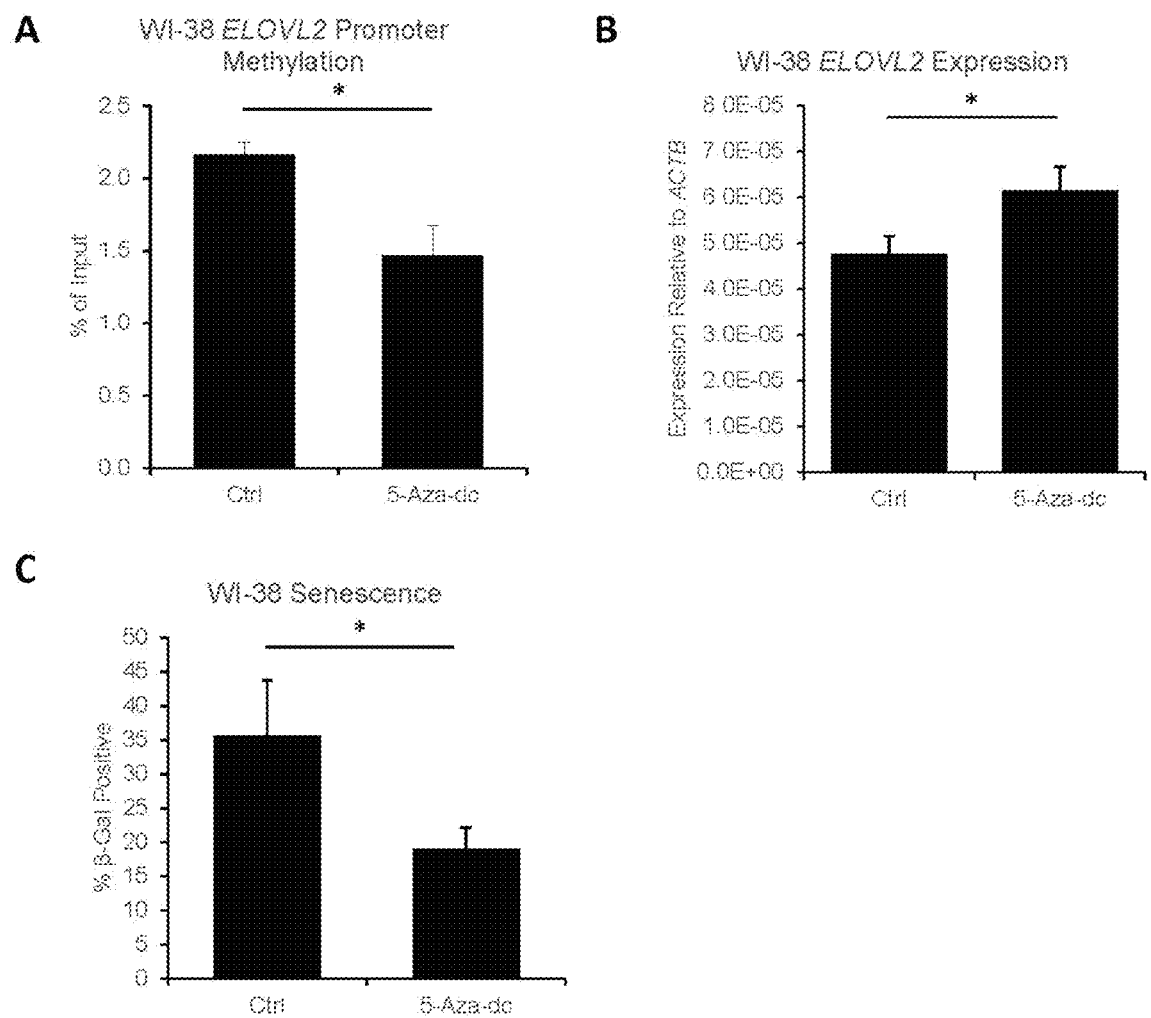
FIGS. 2A-2C show manipulating DNA methylation in PD52 WI-38 cells.

The effect of the ELOVL2 promoter methylation level on ELOVL2 expression was tested. WI-38 fibroblasts were treated with 5-Aza-2'-deoxycytidine (5-Aza-dc), a cytidine analog that inhibits DNA methyltransferase [22]. The cells were treated for 2 days with 2 μM 5-Aza-dc followed by 5 days of culture without the compound. At the end of experiment, the expression of ELOVL2 was measured by qRT-PCR. It was found that upon treatment with 5-Aza-dc, ELOVL2 promoter methylation is reduced (FIG. 2A), while ELOVL2 expression is upregulated (FIG. 2B). Moreover, upon 5-Aza-dc treatment a lower percentage of senescent cells were observed in culture (FIG. 2C). These data suggest that decreasing ELOVL2 promoter methylation positively influences ELOVL2 expression, and apparent age of fibroblasts.

Figures 3A, 3B, 3C, 3D, 3E:
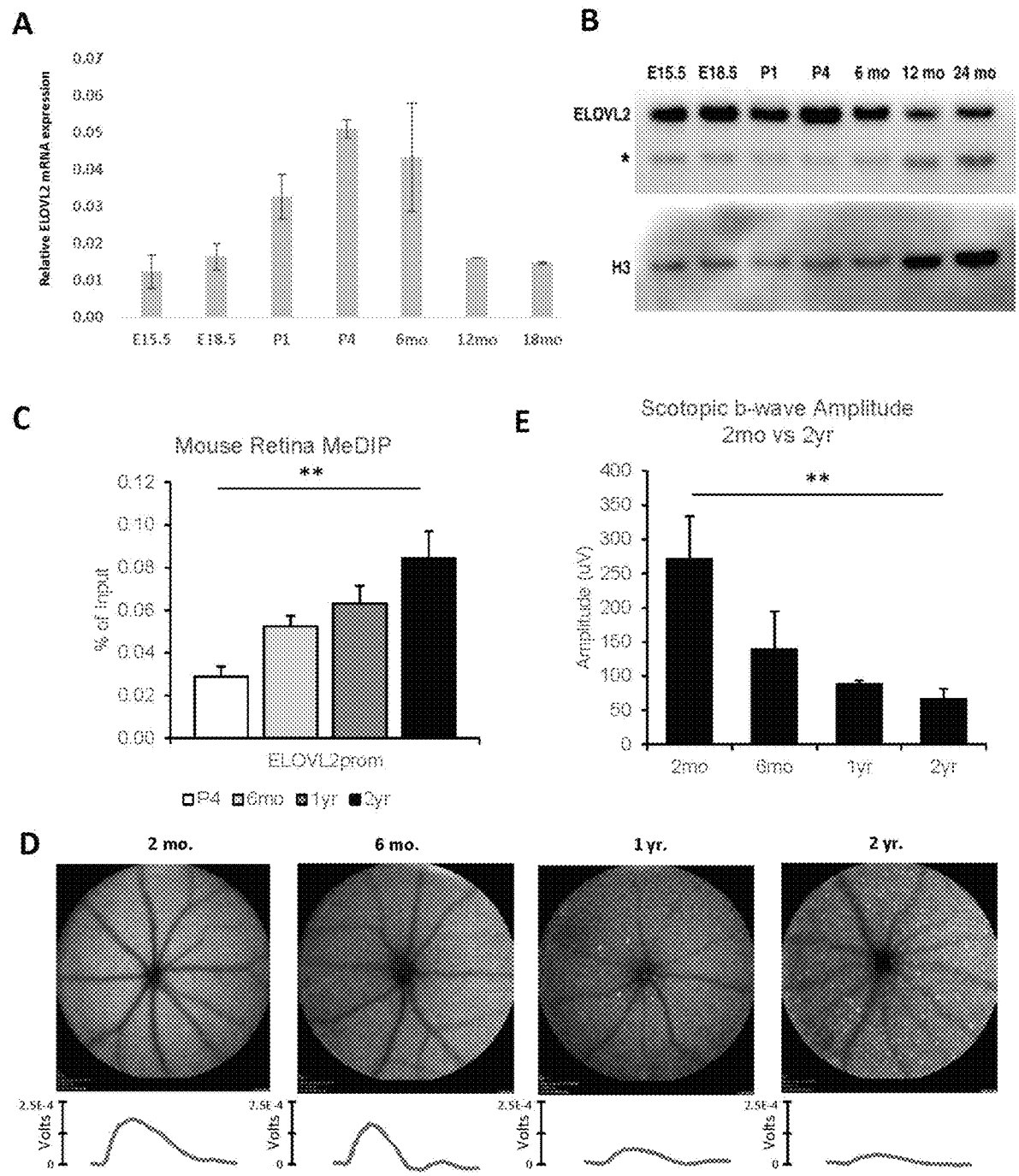
FIGS. 3A-3E show ELOVL2 and the retina.

Vision is among the top predictors of aging. Visual contrast sensitivity score was among the top 5 individual predictors of age relative to 377 variables evaluated [23]. ELOVL proteins are highly expressed in eye, and several of them have been implicated in eye diseases [9, 24]. However, in the methylation model only ELOVL2 contains methylation marks that are highly correlated with age [3]. Therefore, it was investigated whether the expression level of ELOVL2 in wild-type (C57BL/6) mouse retinas changes with age. It was found by qRT-PCR and Western blot that, similar to data from aging human fibroblasts, expression level of ELOVL2 inversely correlates with age of the animal (FIGS. 3A and 3B). Most importantly, MeDIP analysis indicated that ELOVL2 promoter methylation in the retina increases with age of the animal (FIG. 3C).

Figure 9A:
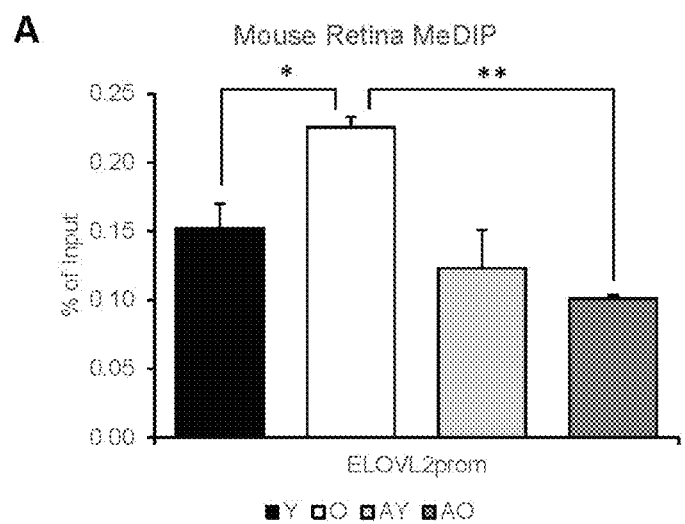
FIGS. 9A-9B.
Figure 9B:
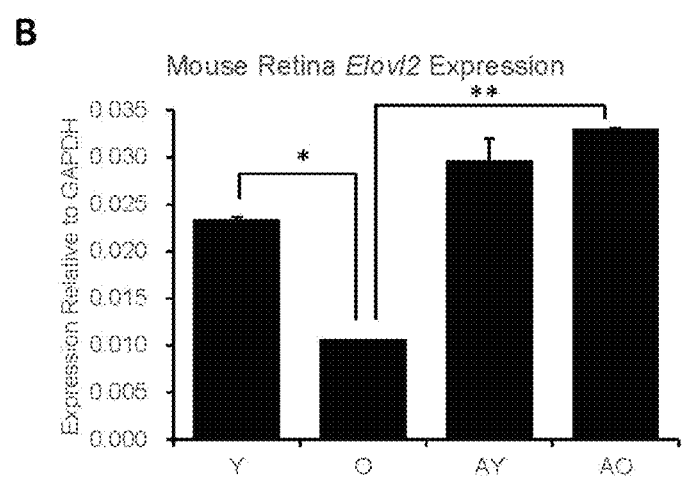

In parallel, the ELOVL2 promoter methylation and mRNA expression levels in the retinas dissected from Ames dwarf mice (Prop1$^{df}$) was investigated, which live significantly longer and exhibit many symptoms of delayed aging compared to wild-type mice [25, 26]. It was found that aged Ames dwarf retinas display lower ELOVL2 promoter methylation and increased expression when compared to aged wild-type mice (FIG. 9). This suggests that ELOVL2 expression and methylation might be indicative of animal health.

Figure 8A:
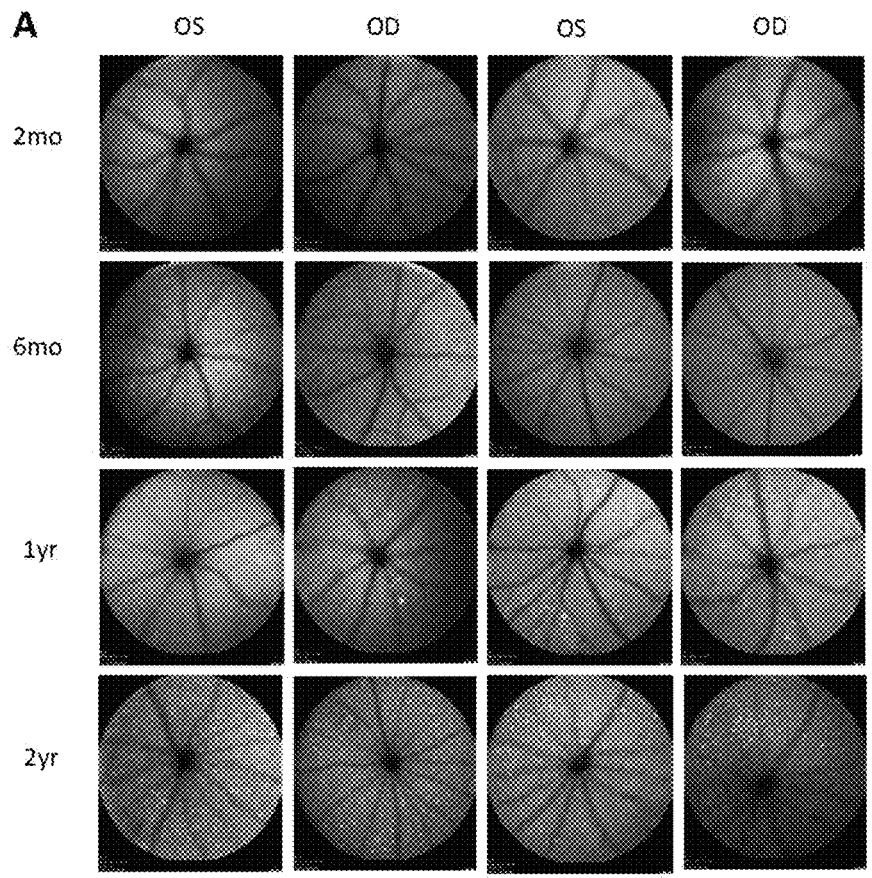
FIGS. 8A-8D show aging characteristics of WT mouse retinas.
Figure 8B:
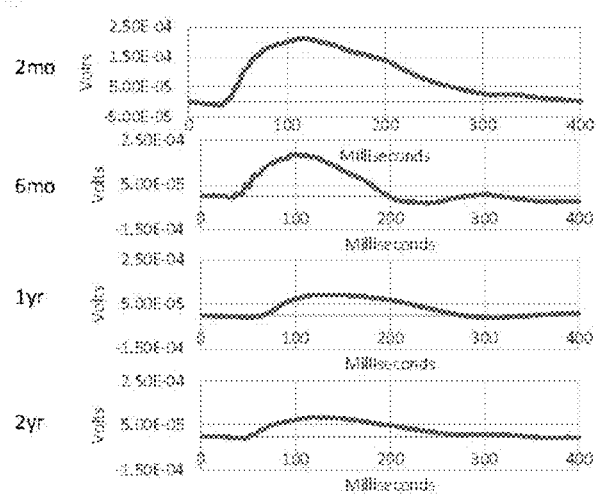
Figure 8C:
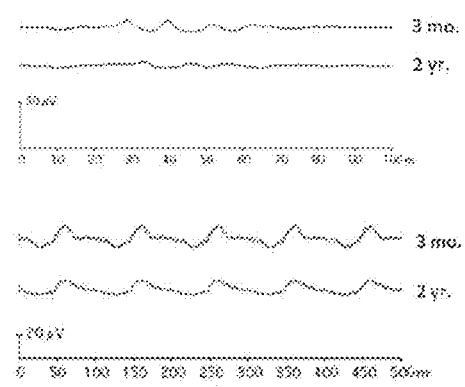
Figure 8D:
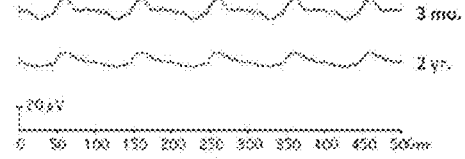

It was evaluated whether visual performance and eye structure change during the studied age span of animal. First, structural changes using fundus autofluorescence imaging of wild-type C57BL/6 mice at the ages of 2 months, 6 months, 1 year, and 2 years was evaluated. It was observed that autofluorescent punctate aggregates begin to appear in the fundus at 1 year of age, and are very pronounced at 2 years of age (FIG. 3D and FIG. 8A). Then to evaluate the visual function of the aging mice, electroretinogram (ERG) analysis was performed. As mice age, the number and sensitivity of rods decreases [27]. Indeed, older mice displayed decreased scotopic response amplitude by ERG (FIGS. 3D and 3E).

Figures 10A, 10B, 10C, 10D, 10E:
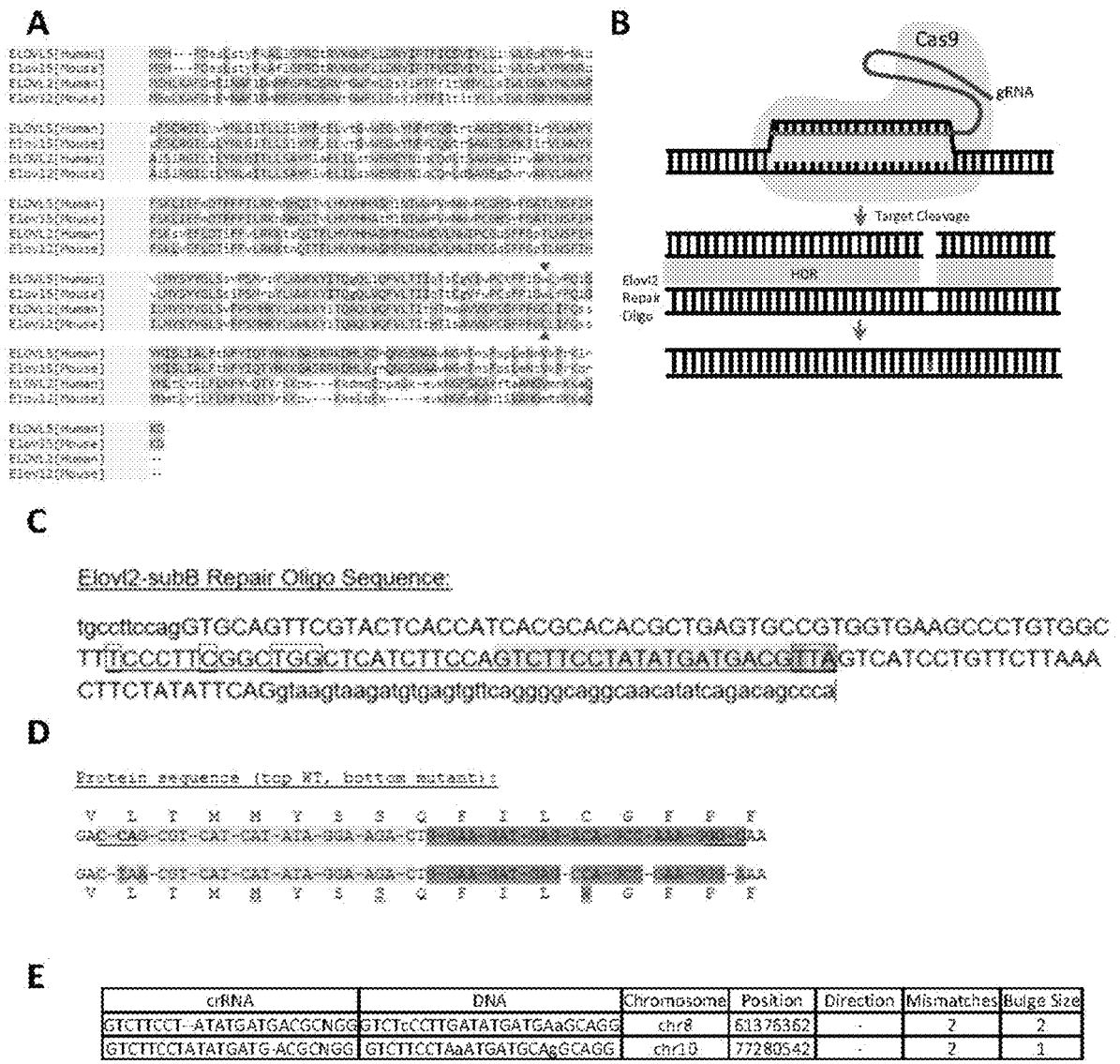
FIGS. 10A-10E show an ELOVL2-ELOVL5 fate-switch mice.

To investigate whether ELOVL2 plays a role in eye aging and visual performance, ELOVL2 mutant C57BL/6 mice was generated using CRISPR-Cas9 paired with homologous recombination. Since the ELOVL2 knockout mice display reductions in fertility [28], instead ELOVL2-mutant mice encoding a cysteine-to-tryptophan substitution (C217W) was generated that has been shown to change the substrate specificity of ELOVL2 to that of ELOVL5, effectively disrupting the unique ability of ELOVL2 to convert the C22 omega-3 PUFA docosapentaenoic acid (DPA) (22:5n-3) to 24:5n-3 [6]. Two gRNAs to target ELOVL2 near codon 217 and a repair donor oligonucleotide was designed with a base pair mutation to generate the mutant C217W, along with silent mutations to disrupt the guide and protospacer-adjacent motif sequence to prevent re-cleavage after editing. The gRNA, repair oligonucleotide, and Cas9 mRNA were injected into C57BL/6N mouse zygotes (FIG. 4A and FIG. 10A-10D). One correctly targeted homozygous founder from one of the gRNAs was identified. No off-target mutations were found (FIG. 10E). C217W homozygous mice developed normally, not displaying any overt phenotypes.

Figure 11A:
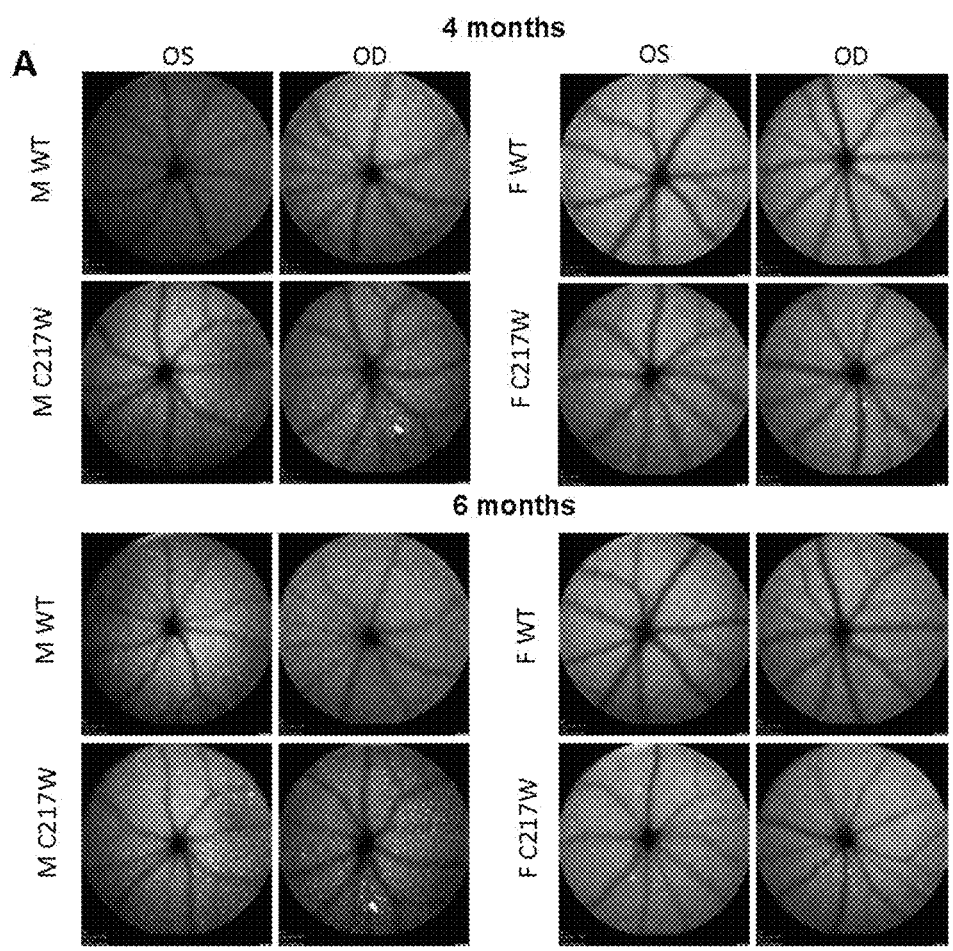
Figure 11A:
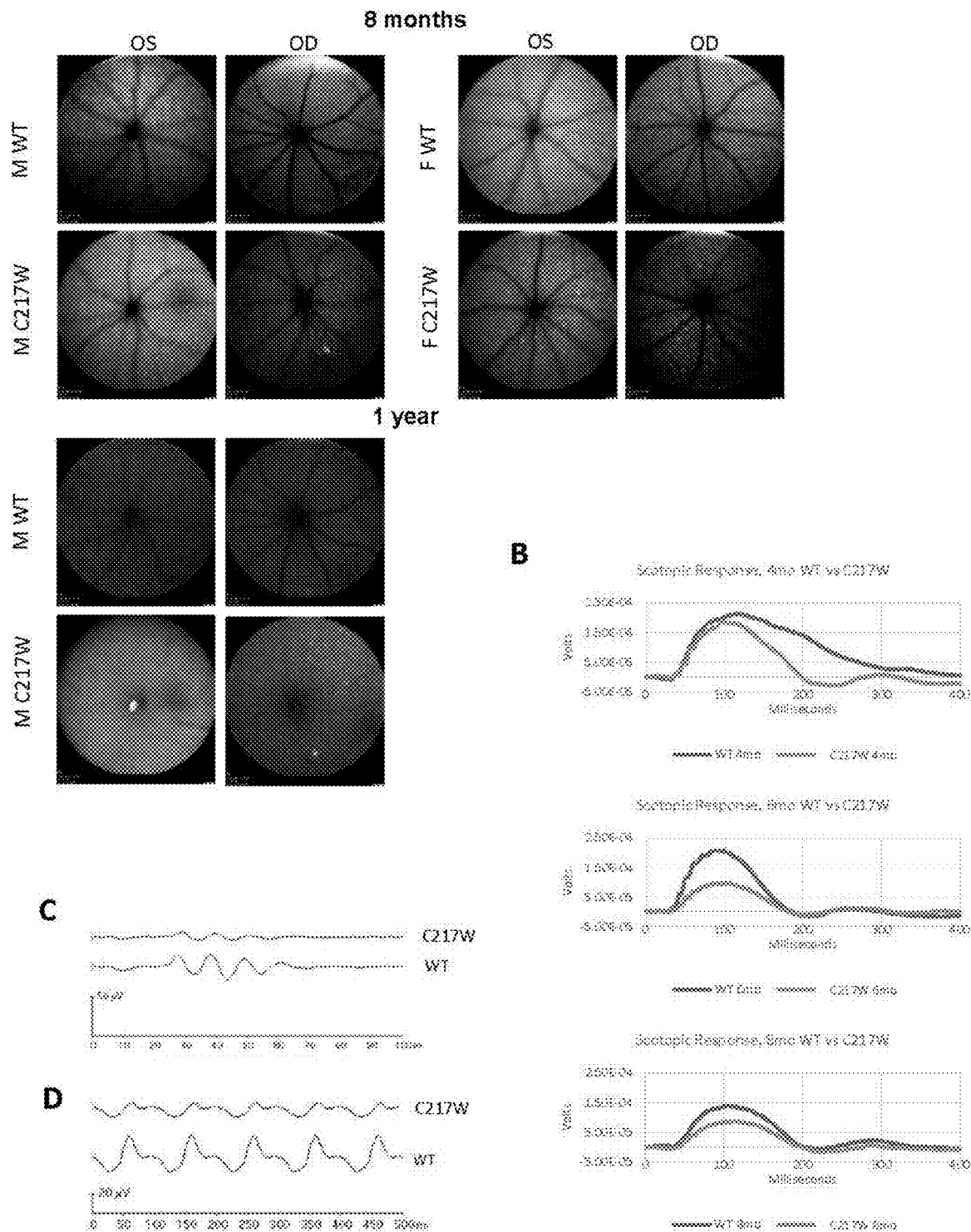
Figure 12A:
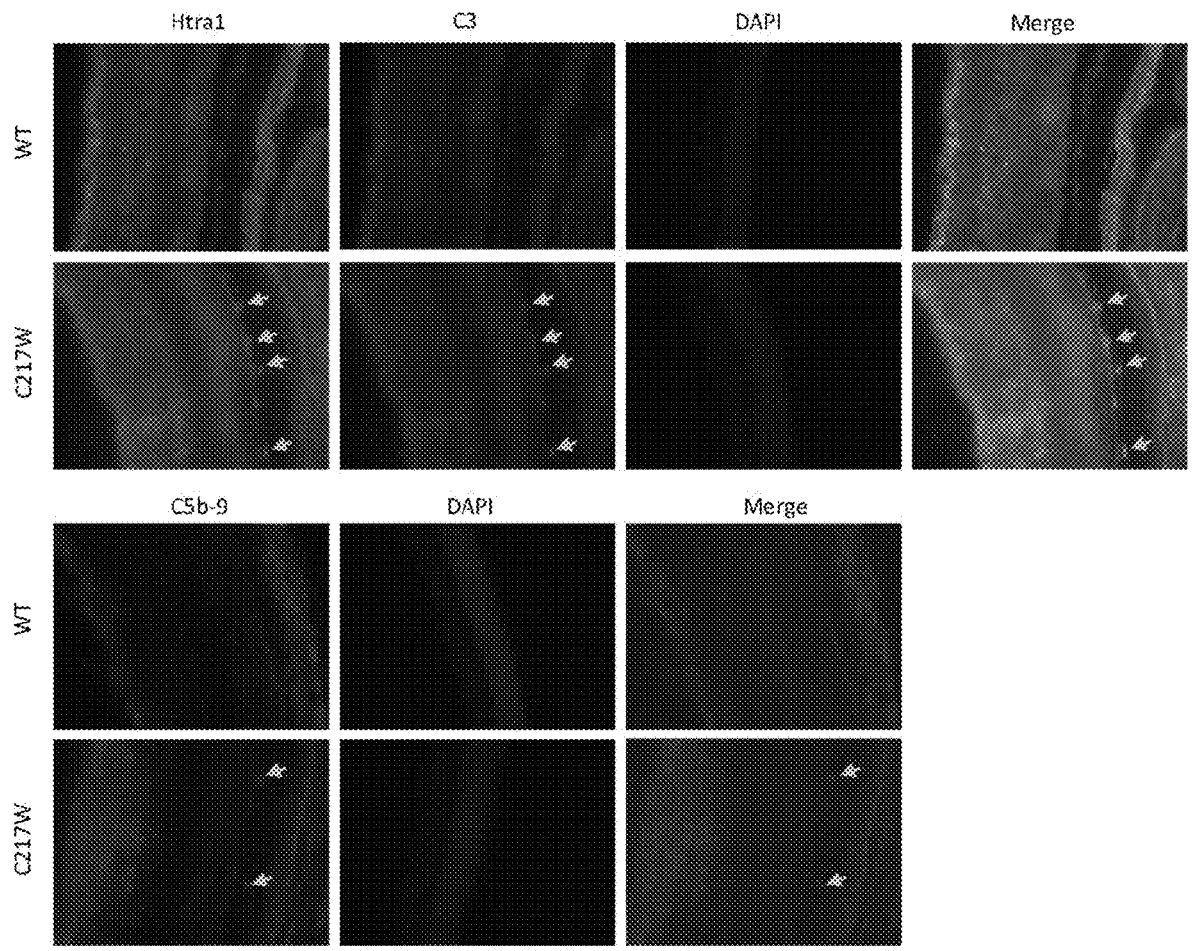
FIGS. 12A-12D show a characterization of drusen-like aggregates.
Figure 12B:
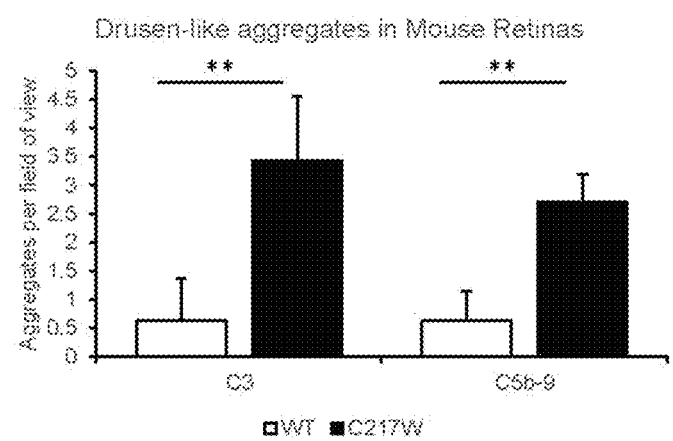
Figure 12C:
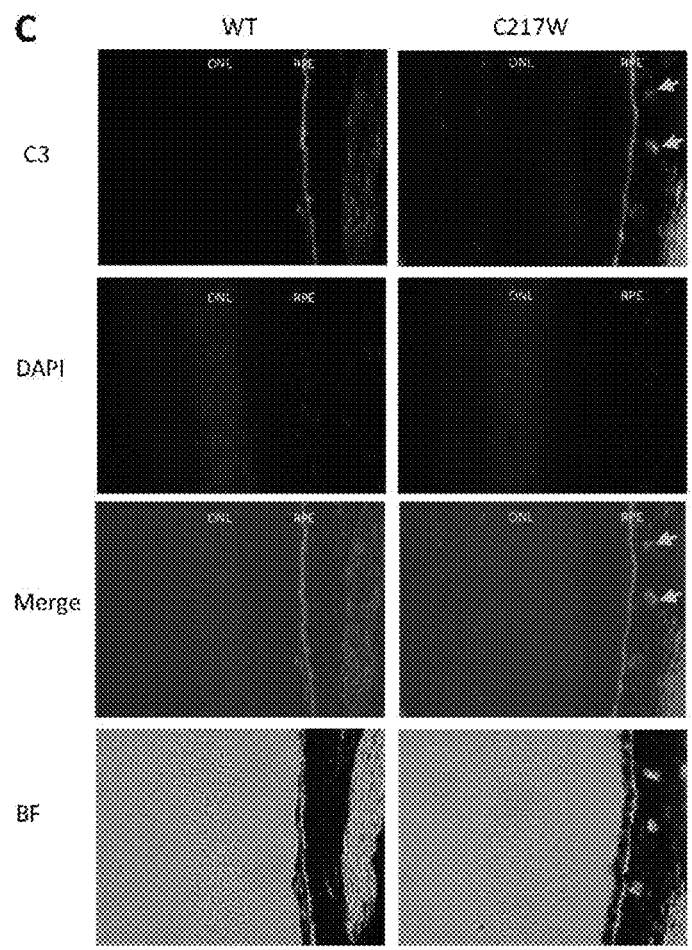
Figure 12D:
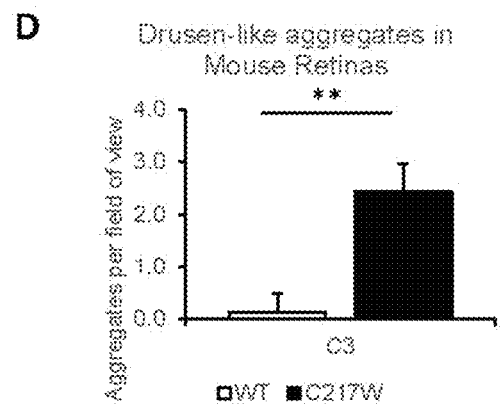

Then it was investigated whether eye structure and visual performance are changed in the C217W mutant. Interestingly, in the ELOVL2 mutant mice, autofluorescent aggregates appear in the fundus at just 6 months of age, much earlier than in wild-type mice (FIG. 4B and FIG. 3D), showing that normal ELOVL2 activity is crucial to maintaining a healthy retina. This phenotype was consistently observed in 4, 6, 8, and 12-month old mutant animals (FIG. 11A).

Figures 4A, 4B, 4C, 4D, 4E:
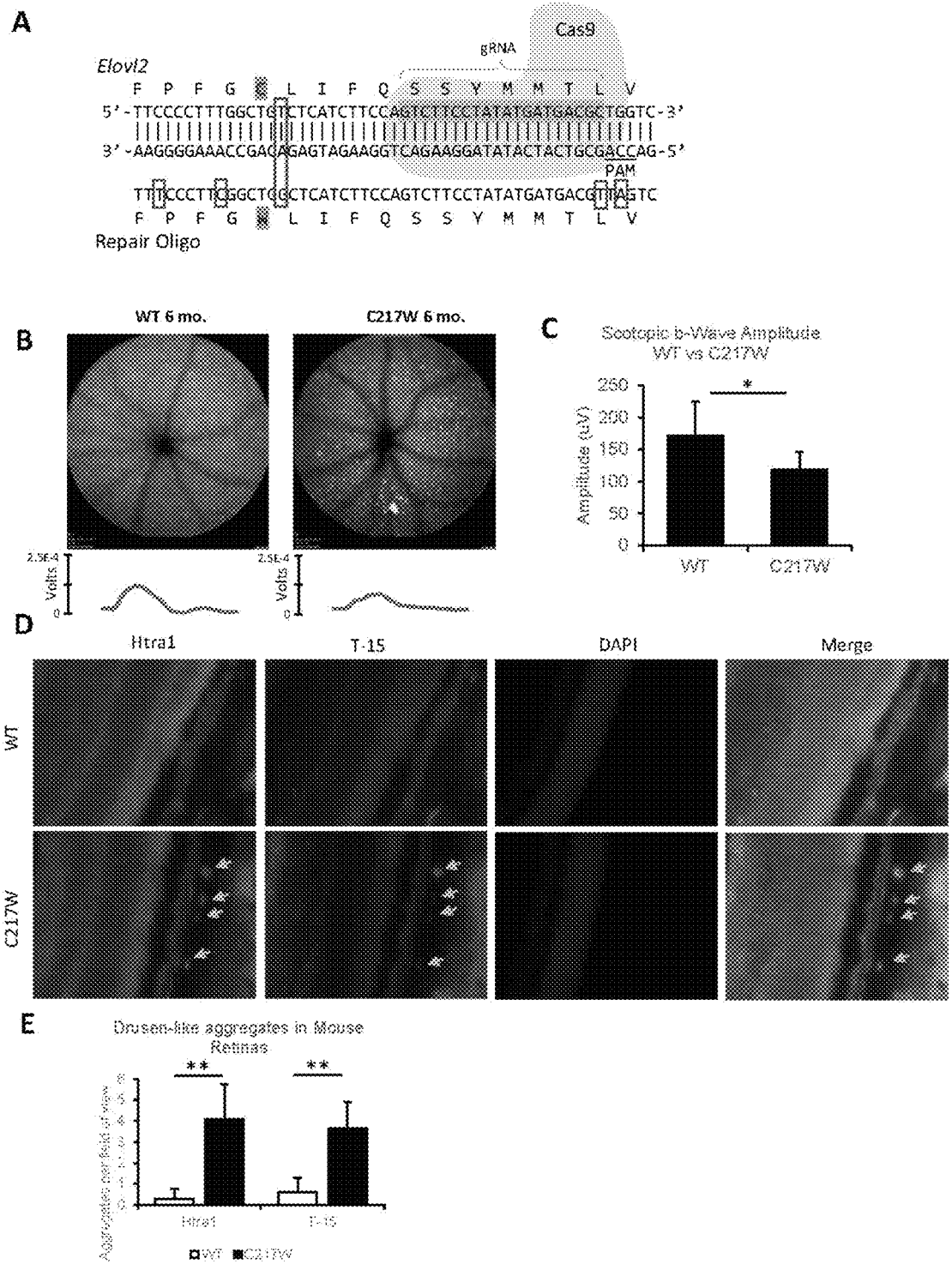
FIGS. 4A-4E show retina phenotypes in ELOVL2 fate-switch mice.

It was then tested the photoreceptor function of these mutant mice using ERG. Compared to wild-type littermates, it was observed a decrease in scotopic response amplitude in C217W mutant mice (FIGS. 4B and 4C). This reduced response was consistently reproduced at other ages (FIG. 11B). Although the most affected signal was scotopic response, other types of ERG measurements were also affected in ELOVL2 mutants, including oscillatory potential and flicker response (FIGS. 11C and 11D).

The retinas of C217W and WT mice were immunostained to investigate whether the aggregates observed as puncta in the autofluorescence fundus imaging were similar to drusen, that in humans are a risk factor for developing AMD [14]. Indeed, the immunostaining detected HTRA1, T-15, C3, and C5b-9 positive aggregates in the C217W retinas only (FIG. 4D, 4E, and FIG. 12). Given the prominence and early development of drusen-like aggregates in the mutant mice, they can potentially be models of AMD.

Figures 5A, 5B, 5C, 5D:
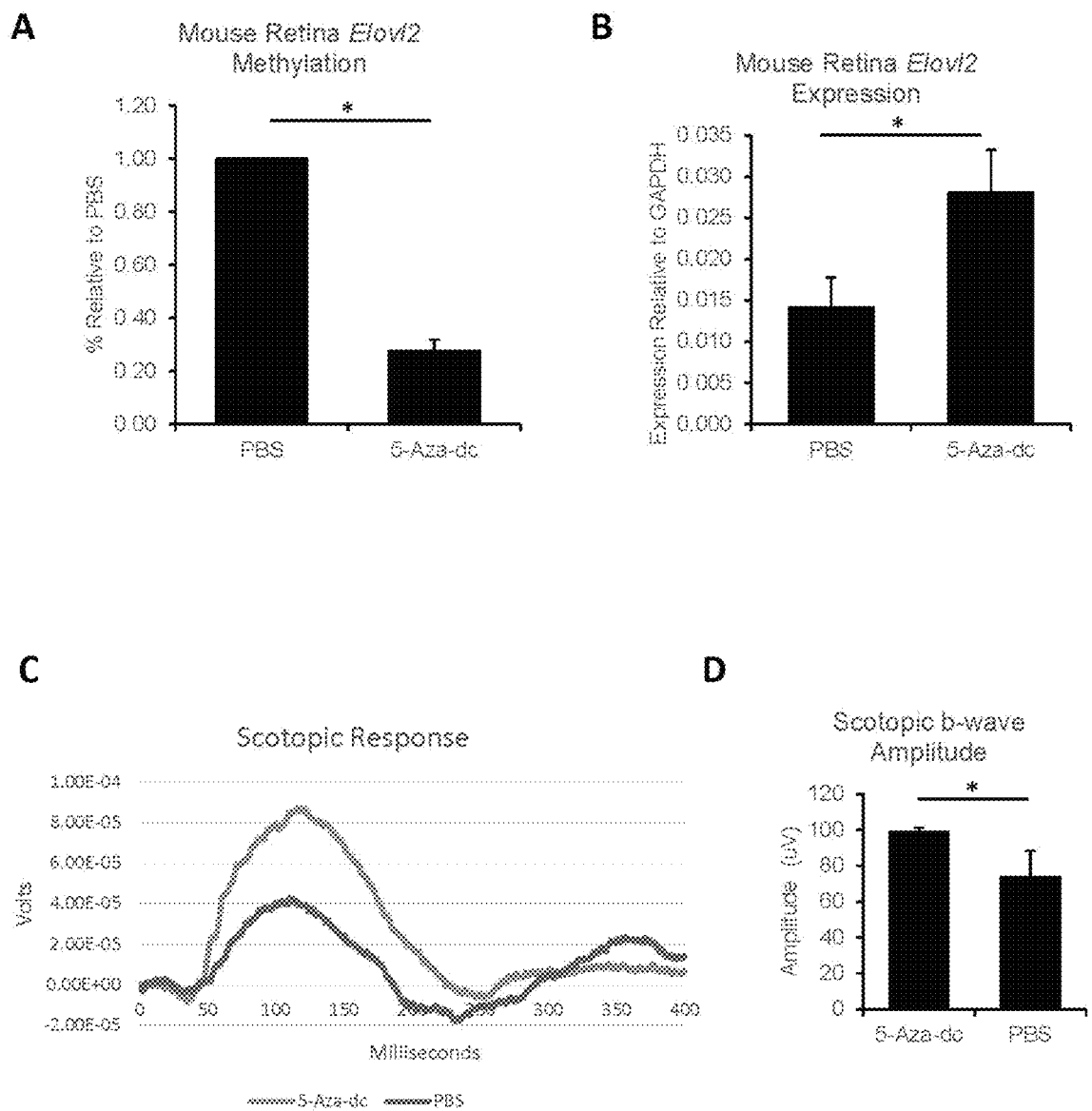
FIGS. 5A-5D show 5-Aza-dc injection in mouse eyes.
Figure 13:
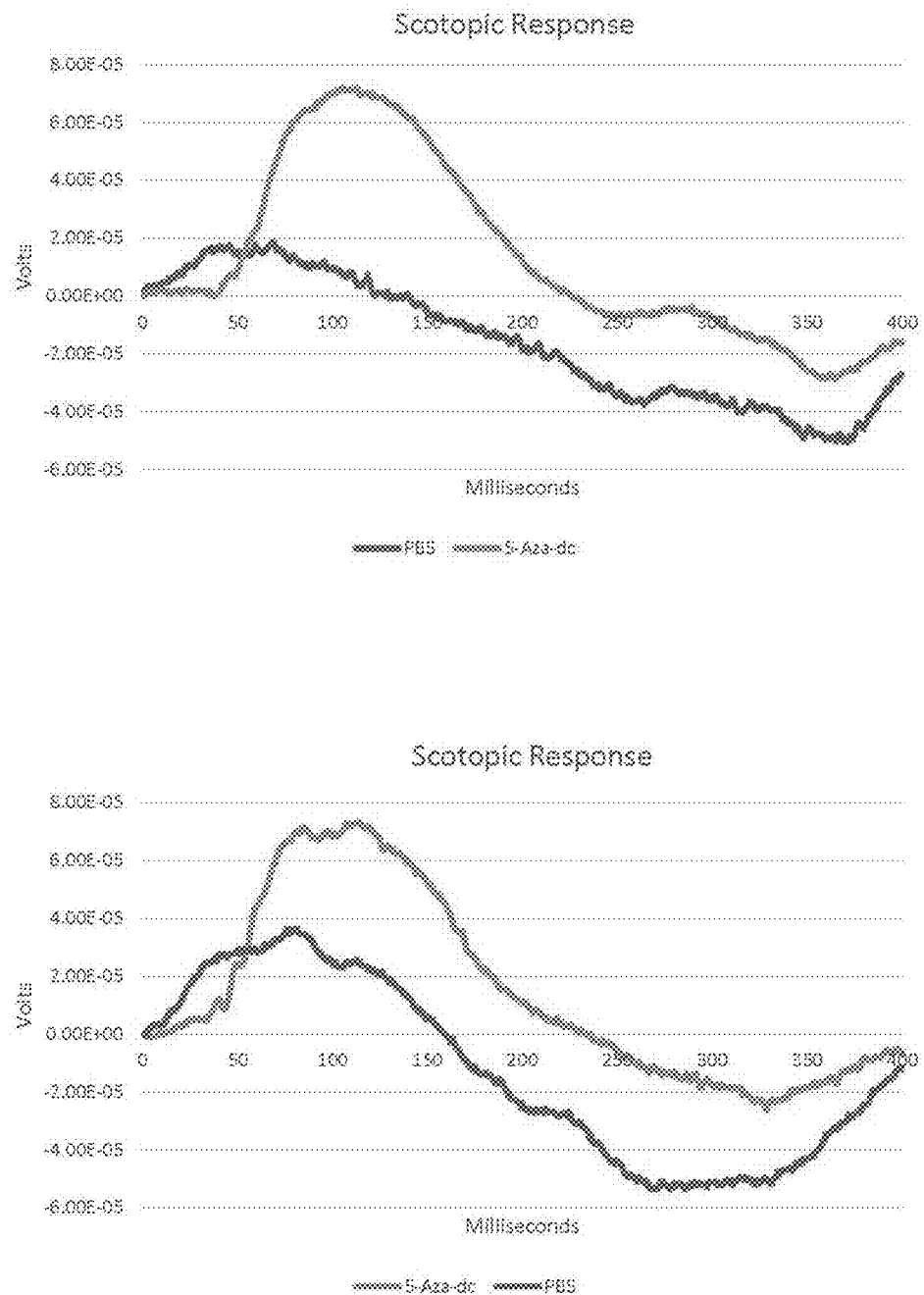
FIG. 13 shows a scotopic response of ERG in mouse eyes injected with PBS and 5-Aza-dc.

Finally, it was investigated whether the aging characteristics in mouse eyes could be reverted by DNA demethylation, including the ELOVL2 promoter. To do that, each mouse was injected with 1 µL of 2 µM 5-Aza-dc in one eye and 1 µL of PBS in the other eye, every other week over a period of 2 months starting at age of 10 months. It was found, using the MeDIP method, that methylation of the ELOVL2 promoter decreased after treatment (FIG. 5A). It was also found that ELOVL2 expression was upregulated in the treated eyes (FIG. 5B). Finally the photoreceptor function was checked by ERG, and it was found that scotopic response was improved in the injected eyes (FIG. 5C and FIG. 13). These data further support ELOVL2 methylation status as a target of aging and use of DNA methyltransferase inhibitors to influence aging eye characteristics.

Human clinical use example: Bi-weekly administration (20 uM) over three months in a patient with dry AMD A 75 year old female with bilateral, dry age-related macular degeneration (AMD) is seen in an ophthalmology clinic. She is otherwise healthy. She consents to an experimental study comparing demethylation therapy verses control. At baseline both eyes show a similar level of AMD as evidenced by clinical assessments for visual acuity, size of geographic atrophy as measured by autofluorescence, optical coherence tomography, and scotopic response on electroretinography. The patient is treated with 100 uL of decitabine (20 uM) formulated as a sterile, isotonic, pH buffered solution administered by intravitreal injection in her left eye (active treatment). She receives 100 ul of the same sterile, isotonic, pH buffered solution but without decitabine administered by intravitreal injection in her right eye (control treatment). Immediately following the administration of the active and control treatments, a sample of intravitreal fluid is withdrawn from each eye for baseline measurements of ELOVL2 expression and methylation level. It is observed that ELOVL2 is hypermethylated to a similar extent in both eyes. The levels of ELOVL2 expression are also similar and a low level of expression is observed in both eyes. Both the active and control treatments are continued in the left and right eyes respectively with administrations every other week for 3 months. Both the active and control treatments are equally well tolerated over the period of administration. Immediately following the last administration, samples of intravitreal fluid are obtained from both eyes for measurement of ELOVL2 gene expression and methylation. The same clinical assessments for geographic atrophy performed at baseline are repeated for each eye. Significant differences are observed between the eye treated with decitabine compared to control. In the decitabine treated eye, ELOVL2 methylation is reduced by almost 30% and ELOVL2 gene expression is increased also by about 30% compared to baseline. Also, the scotopic response is increased by about 30% over baseline. In addition, there is no progression of the growth of geographic atrophy as measured by fundus autofluorescence compared to baseline. In marked contrast, there is no observable change in the control eye in any of the other parameters. Gene methylation and gene expression and scotopic response values remain similar to those observed at baseline values. The patient returns to the clinic for a follow up visit at 6 months. Clinical assessment reveals the improvement in scotopic response in the eye treated with decitabine is sustained showing about a 20%-30% improvement over baseline. Scotopic response in the control eye remains similar to the baseline value.

Human clinical use example: Administration (15 uM) once monthly for 12 months in a patient with Geographic Atrophy A 65 year old male with dry age-related macular degeneration (AMD) with Geographic Atrophy is seen in an ophthalmology clinic. His vision as assessed by scotopic response is declining. His area of geographic atrophy as measured by fundus autofluorescence over the last 2 years shows steady progression. He is otherwise healthy. The patient is treated with 100 uL of decitabine (15 uM) formulated as a sterile, isotonic, pH buffered solution administered by intravitreal injection. An intravitreal sample withdrawn immediately after decitabine administration reveals hypermethylation of the ELOVL2 promotor and a low level of ELOVL2 expression. The decitabine treatment is continued with the same dose administered every 5 weeks over a 12 month period. The administrations are well tolerated with no adverse effects observed. Following the last decitabine administration a sample of vitreous fluid is obtained and tested for ELOVL2 gene methylation and ELOVL2 gene expression. The studies reveal ELOVL2 methylation has decreased by almost 60% (from baseline) and ELOVL2 gene expression is increased by about 50% (over the baseline value). The patient's scotopic response is markedly improved and is about 30% increased over baseline. There is no geographic atrophy growth as measured by fundus autofluorescence.

Human Clinical use Example: ELOVL2 Gene Therapy

A 70 year old male with dry age-related macular degeneration (AMD) with Geographic Atrophy is seen in an ophthalmology clinic. His vision as assessed by scotopic response has been steadily declining. His area of geographic atrophy as measured by fundus autofluorescence shows steady progression. He is otherwise healthy and consents to treatment using ELOVL2 gene therapy. One week prior to the gene therapy procedure he is started on oral prednisone (0.5 mg/kg). A recombinant adeno-associated viral vector with the ELOVL2 coding sequence is created and packaged under good medical practice guidelines. It is suspended in a buffered saline solution at a titer of $1.5 \times 10^{11}$ genomes in 0.3 ml aliquots. After one week on oral prednisone, a standard vitrectomy is performed to remove cortical vitreous using standard vitreoretinal techniques under general anesthesia. The patient is then administered 0.3 ml of a buffered saline solution containing a titer of $1.5 \times 10^{11}$ genomes in total injected in the subretinal space using a specialized subretinal cannula just outside of the macula. An air fluid exchange is performed and wounds are sutured in a standard fashion. The patient is continued on oral prednisone (0.5 mg/kg), with a slow taper to finish 4 weeks post surgery. Analysis of cells obtained from the vitreous sample reveal a low level of ELOVL2 expression. Follow-up at 6 months and at one year following the gene therapy procedure show there is no significant progression in the area of geographic atrophy as measured by fundus autofluorescence and vision as assessed by scotopic response is improved by about 20% to about 30%.

Discussion

Previous studies have revealed a highly significant correlation between ELOVL2 promoter methylation and age in humans [3, 29, 30]. In the current study, it was investigated whether ELOVL2 methylation and expression plays a role in aging phenotypes of human fibroblast and mouse retina models.

WI-38 fibroblasts were isolated by Hayflick and Moorhead in the 1960s, and were observed to gradually experience signs of senescence as they divided, first slowing then stopping their division at 50+/−10 population doublings, a phenomenon which would later become known as the Hayflick limit [31]. In addition, cells were found to senesce in vivo with increasing age [32], and primary cells from different species were found to have a maximum in vitro lifespan correlated with the maximum lifespan of the species [33]. It was found that in addition to these changes, ELOVL2 expression decreases with increasing passage number in human fibroblasts. Because promoter methylation is generally inversely correlated with expression, it was expected that promoter methylation would increase with cellular aging and found this to be true. Because of the decreasing expression in cells and increasing promoter methylation in both cells and humans with age, it was hypothesized that knocking down ELOVL2 would result in advanced aging phenotypes. Indeed, cells treated with shRNA directed against ELOVL2 showed decreased ELOVL2 expression, decreased proliferative capacity, increased senescence, and an age-related change in morphology compared to control cells.

To further investigate aging phenotypes, ELOVL2 mutant mice were created. Using CRISPR-Cas9, a C217W mutation was generated, shown previously to switch the substrate specificity of the ELOVL2 catalytic site to the equivalent of ELOVL5, effectively disrupting the unique ability of ELOVL2 to convert the C22 omega-3 PUFA docosapentaenoic acid (DPA) (22:5n-3) to 24:5n-3[6]. Both ELOVL2 and ELOVL5 have been found to elongate eicosapentaenoic acid (EPA; 20:5n-3) to docosapentaenoic acid (DPA; 22:5n-3), but only ELOVL2 is known to further elongate DPA to 24:5n-3, the penultimate precursor of DHA [6]. Therefore the health of the eyes of the ELOVL2 mutant mice was investigated.

The presence of protein aggregates on the retina at 6 months of age was oberved, compared to 1 year in wild-type mice by autofluorescence imaging. Retina sections were stained for oxidized phosphocholine (with T-15 antibody), HTRA1, C3, and C5b-9, all proteins found in drusen, which are commonly found in patients with age-related macular degeneration (AMD).

Photoreceptor function was assessed by ERG. ERG measures the electrical signals produced by the retina in response to light stimulus, and so can detect functional abnormalities of photoreceptors. Because the mouse retina contains mostly rod photoreceptors, the functional differences in their electrical signals (scotopic response) are most relevant in assessing visual performance. Besides scotopic response, cone response and 10 Hz flicker was also investigated. All of these signals, but most notably scotopic response, decreased in amplitude both with age in wild-type mice and in mutant mice compared to age-matched littermates. Together with the presence of drusen-like aggregates, these indicators of decreased photoreceptor function are signs of AMD. Therefore, it was concluded that ELOVL2 function is crucial for preventing early onset of drusen-like aggregates and maintaining healthy photoreceptor function in mice. Combined with the accelerated appearance of drusen-like aggregates, the loss of photoreceptor function in ELOVL2 mutant mice shows that ELOVL2 is an important part of maintaining a healthy retina through old age in mice. In addition, it was found that ELOVL2 plays an important role in influencing aging phenotypes in human cells and could potentially be influencing the process of aging on a broader level.

It was found that the ELOVL2 C217W mice presented with drusen-like aggregates and decreased photoreceptor sensitivity at a significantly earlier stage than either of the control littermates. It was concluded that the ELOVL2 C217W mutation is responsible for the accelerated eye aging phenotype. Taken together, the present study shows evidence that ELOVL2 plays a role in aging characteristics, and in particular, eye function. Further, the level of methylation at the promoter region of ELOVL2 is correlated with its expression and can be altered to potentially influence aging characteristics.

Methods

Cell Culture and Treatment.

WI-38 and IMR-90 human fibroblasts were cultured in EMEM (ATCC) supplemented with 10% fetal bovine serum (Omega) and 1% penicillin/streptomycin (Gibco), and kept in a humidified incubator at 5% $CO_2$ and 37° C. Confluence was calculated via ImageJ imaging software, including 3 fields of view per sample (10×). Upon confluence, cells were split and seeded at a 1:3 ratio. Population doublings (PD) were calculated by cell count. Knockdown lentivirus was generated using MISSION shRNA (Sigma) according to the manufacturer's instructions. 5-Aza-2'-deoxycitidine was purchased from TSZ Chem (CAS #2353-33-5), and dissolved in cell culture medium at a concentration of 2 µM. Cells were treated for a period of 48 hours. The medium was then replaced with regular cell culture medium, and the cells were cultured for 5 more days.

Senescence-associated β-galactosidase (SA-β-gal) Activity.

The SA-β-gal activity in cultured cells was determined using the Senescence β-Galactosidase Staining Kit (Cell Signaling Technology), according to the manufacturer's instructions. Cells were stained with DAPI afterwards, and percentages of cells that stained positive were calculated with imaging software (Keyence), including 3 fields of view (10×).

Nucleic Acid Analysis.

DNA and RNA were isolated from human fibroblasts and mouse tissues with TRIzol (Ambion) according to manufacturer's instructions. RNA was converted to cDNA with iScript cDNA Synthesis Kit (Bio-Rad). qPCR was performed using SsoAdvanced Universal SYBR Green Supermix (Bio-Rad).

Methylated DNA Immunoprecipitation (MeDIP) was performed by shearing 1 µg DNA by Bioruptor (Diagenode) for 8 cycles on the high setting, each cycle consisting of 30 seconds on and 30 seconds off. Sheared DNA was denatured, incubated with 1 µg 5 mC antibody MABE146 (Millipore) for 2 hours, then with SureBeads protein G beads (Bio-Rad) for 1 hour. After washing, DNA was purified with QIAquick PCR Purification Kit (Qiagen). qPCR was then performed as above.

Western Blotting.

10 µg of total protein isolated with TRIzol (Ambion) from retinas of WT mice of varying stages of development was subject to SDS-PAGE. Western blotting was performed using a well-accepted protocol (see Table 2 for antibodies used in the study). ELOVL2 protein expression level was normalized to H3.

CRISPR-Cas9 Design.

CRISPR-Cas9 reagents were generated essentially as previously described [34]. T7 promoter was added to cloned Cas9 coding sequence by PCR amplification. The T7-Cas9 product was then gel purified and used as the template for in vitro transcription (IVT) using mMESSAGE mMACHINE T7 ULTRA kit (Life Technologies). T7 promoter and sgRNA sequence was synthesized as a long oligonucleotide (Ultramer, IDT) and amplified by PCR. The T7-sgRNA PCR product was gel purified and used as the template for IVT using the MEGAshortscript T7 kit (Life Technologies). A repair template encoding the C217W variant was synthesized as a single stranded oligonucleotide (Ultramer, IDT) and used without purification. Potential off-targets were identified using Cas-OFFinder35, selecting the targets with fewest mismatches (http://www.rgenome.net/cas-offinder/). The founder mouse and all F1 mice were sequenced for off-targets.

Animal Injection and Analysis.

All animal procedures were conducted with the approval of the Institutional Animal Care Committee at the University of California, San Diego. C57BL/6N mouse zygotes were injected with CRISPR-Cas9 constructs. Oligos were injected into the cytoplasm of the zygotes at the pronuclei stage. Mice were housed on static racks in a conventional animal facility, and were fed ad libitum with Teklad Global 2020X diet. For the 5-Aza-dc injection study, mice were anesthetized by intraperitoneal injection of ketamine/xylazine (100 mg/kg and 10 mg/kg, respectively), and given an analgesic eye drop of Proparacaine (0.5%, Bausch & Lomb). Animals were intraocularly injected with 1 µL of PBS in one eye, and 1 µL of 2 µM 5-Aza-dc dissolved in PBS in the contralateral eye, every other week over a period of 2 months.

Electroretinograms (ERGs) were performed following a previously reported protocol [36]. Briefly, mice were dark-adapted for 12 h, anesthetized with a weight-based intraperitoneal injection of ketamine/xylazine, and given a dilating drop of Tropicamide (1.5%, Alcon) as well as a drop of Proparacaine (0.5%, Bausch & Lomb) as analgesic. Mice were examined with a full-field Ganzfeld bowl setup (Diagnosys LLC), with electrodes placed on each cornea, with a subcutaneous ground needle electrode placed in the tail, and a reference electrode in the mouth (Grass Telefactor, F-E2). Lubricant (Goniovisc 2.5%, HUB Pharmaceuticals) was used to provide contact of the electrodes with the eyes. Amplification (at 1-1,000 Hz bandpass, without notch filtering), stimuli presentation, and data acquisition are programmed and performed using the UTAS-E 3000 system (LKC Technologies). For scotopic ERG, the retina was stimulated with a xenon lamp at −2 and −0.5 log cd·s/m2. For photopic ERG, mice were adapted to a background light of 1 log cd·s/m2, and light stimulation was set at 1.5 log cd·s/m2. Recordings were collected and averaged in manufacturer's software (Veris, EDI) and processed in Excel.

Mouse Retina Analysis.

Retinas were collected immediately after sacrificing mice, fixed in 4% paraformaldehyde for 1 hour, and stored in PBS at 4° C. For immunostainings, retinas were sectioned, mounted on slides, then incubated with 5% BSA, 0.1% Triton-X PBS blocking solution for 1 hour. Primary antibodies (see Table 2 for antibodies used in the study) were added 1:50 in 5% BSA PBS, and incubated at 4° C. for 16 hours. Following 3×PBS wash, secondary antibodies were added 1:1000 in 5% BSA PBS for 30 minutes at room temperature. Samples were then washed 3× with PBS, stained with DAPI for 5 minutes at room temperature, mounted, and imaged (Keyence BZ-X700).

TABLE 1

List of primers used in the study.

| Off-target checking | Sequence (5'->3') | SEQUENCE |
|---|---|---|
| chr8 off-targ F | GTAATTCCGTGATCACCGTC | SEQ ID NO: 1 |
| chr8 off-targ R | CCAATAAATAACAGCAGAAG | SEQ ID NO: 2 |
| chr10 off-targ F | CAATATGCTCATCATTGTCT | SEQ ID NO: 3 |
| chr10 off-targ R | CCACACATGTCTACCTTCCT | SEQ ID NO: 4 |
| MeDIP primers | | |
| hELOVL2 prom. F | CGATTTGCAGGTCCAGCCG | SEQ ID NO: 5 |
| hELOVL2 prom. R | CAGCGGGTGGGTATTCCTG | SEQ ID NO: 6 |
| hACTB prom. F | CTAGGTGTGGACATCTCTTG | SEQ ID NO: 7 |
| hACTB prom. R | TGCAGGAGCGTACAGAA | SEQ ID NO: 8 |
| mELOVL2 prom. F | AGCTCCTCCGCTACTC | SEQ ID NO: 9 |
| mELOVL2 prom. R | CCAGCCCTTGGTCATC | SEQ ID NO: 10 |
| mACTB prom. F | TAGGCCCAGATGTACAGGAA | SEQ ID NO: 11 |
| mACTB prom. R | CCAGAATGCAGGCCTAGTAA | SEQ ID NO: 12 |
| qPCR primers | | |
| hELOVL2 F | GCGGATCATGGAACATCTAA | SEQ ID NO: 13 |
| hELOVL2 R | CCAGCCATATTGAGAGCAGA | SEQ ID NO: 14 |
| hACTB F | CACCATTGGCAATGAGCGGTTC | SEQ ID NO: 15 |
| hACTB R | AGGTCTTTGCGGATGTCCACGT | SEQ ID NO: 16 |

TABLE 2

LIST OF ANTIBODIES USED IN THE STUDY.

| | Company, Cat# | RRID |
|---|---|---|
| Immunostaining | | |
| TEPC 15 | Sigma M1421 | AB_1163630 |
| HtrA | Santa Cruz sc-377050 | |
| C3 | Santa Cruz sc-58926 | AB_1119819 |
| C5-b9 | Santa Cruz sc-66190 | AB_1119840 |
| MeDIP | | |
| 5-methylcytosine Western blot | Millipore MABE146 | AB_10863148 |
| ELOVL2 | Santa Cruz sc-54874 | AB_2262364 |
| Histone H3 | Cell Signaling 9715 | AB_331563 |

REFERENCES

1. Glei, D. A. et al. Predicting Survival from Telomere Length versus Conventional Predictors: A Multinational Population-Based Cohort Study. PloS One 11, e0152486 (2016).
2. Health, C. O. on S. and. Smoking and Tobacco Use; Surgeon General's Reports; 2004. Smoking and Tobacco Use Available at: http://www.cdc.gov/tobacco/data_statistics/sgr/2004/. (Accessed: 14 Nov. 2014)
3. Hannum, G. et al. Genome-wide Methylation Profiles Reveal Quantitative Views of Human Aging Rates. Mol. Cell 49, 359-367 (2013).
4. Gross, A. M. et al. Methylome-wide Analysis of Chronic HIV Infection Reveals Five-Year Increase in Biological Age and Epigenetic Targeting of HLA. Mol. Cell 62, 157-168 (2016).
5. Leonard, A. E. et al. Identification and expression of mammalian long-chain PUFA elongation enzymes. Lipids 37, 733-740 (2002).

6. Gregory, M. K., Cleland, L. G. & James, M. J. Molecular basis for differential elongation of omega-3 docosapentaenoic acid by the rat ELOVL5 and ELOVL2. J. Lipid Res. 54, 2851-2857(2013).
7. Tikhonenko, M. et al. Remodeling of Retinal Fatty Acids in an Animal Model of Diabetes: A Decrease in Long-Chain Polyunsaturated Fatty Acids Is Associated With a Decrease in Fatty Acid Elongases ELOVL2 and ELOVL4. Diabetes 59, 219-227 (2010).
8. Bazan, N. G., Molina, M. F. & Gordon, W. C. Docosahexaenoic Acid Signalolipidomics in Nutrition: Significance in Aging, Neuroinflammation, Macular Degeneration, Alzheimer's, and Other Neurodegenerative Diseases. Annu. Rev. Nutr. 31, 321-351 (2011).
9. Agbaga, M.-P. et al. Role of Stargardt-3 macular dystrophy protein (ELOVLL4) in the biosynthesis of very long chain fatty acids. Proc. Natl. Acad. Sci. 105, 12843-12848 (2008).
10. Harkewicz, R. et al. Essential Role of ELOVLL4 Protein in Very Long Chain Fatty Acid Synthesis and Retinal Function. J. Biol. Chem. 287, 11469-11480 (2012).
11. Beatty, S., Koh, H., Phil, M., Henson, D. & Boulton, M. The role of oxidative stress in the pathogenesis of age-related macular degeneration. Surv. Ophthalmol. 45, 115-134 (2000).
12. Hollyfield, J. G. et al. Oxidative damage-induced inflammation initiates age-related macular degeneration. Nat. Med. 14, 194-198 (2008).
13. Curcio, C. A., Johnson, M., Huang, J.-D. & Rudolf, M. Apolipoprotein B-containing lipoproteins in retinal aging and age-related macular degeneration. J. Lipid Res. 51, 451-467 (2010).
14. Crabb, J. W. et al. Drusen proteome analysis: An approach to the etiology of age-related macular degeneration. Proc. Natl. Acad. Sci. 99, 14682-14687 (2002).
15. Shaw, P. X. et al. Natural antibodies with the T15 idiotype may act in atherosclerosis, apoptotic clearance, and protective immunity. J. Clin. Invest. 105, 1731-1740 (2000).
16. Shaw, P. X. et al. Complement factor H genotypes impact risk of age-related macular degeneration by interaction with oxidized phospholipids. Proc. Natl. Acad. Sci. U.S.A. 109, 13757-13762 (2012).
17. Cameron, D. J. et al. HTRA1 variant confers similar risks to geographic atrophy and neovascular age-related macular degeneration. Cell Cycle Georget. Tex 6, 1122-1125 (2007).
18. Sivaprasad, S. & Chong, N. V. The complement system and age-related macular degeneration. Eye 20, 867 (2006).
19. Pignolo, R. J., Rotenberg, M. O. & Cristofalo, V. J. Alterations in contact and density-dependent arrest state in senescent WI-38 cells. In Vitro Cell. Dev. Biol. Anim. 30A, 471-476 (1994).
20. Schäuble, S. et al. Quantitative Model of Cell Cycle Arrest and Cellular Senescence in Primary Human Fibroblasts. PLoS ONE 7, e42150 (2012).
21. Jones, P. L. et al. Methylated DNA and MeCP2 recruit histone deacetylase to repress transcription. Nat. Genet. 19, 187-191 (1998).
22. Momparler, R. L. Pharmacology of 5-Aza-2'-deoxycytidine (decitabine). Semin. Hematol. 42, S9-16 (2005).
23. Swindell, W. R. et al. Indicators of 'Healthy Aging' in older women (65-69 years of age). A data-mining approach based on prediction of long-term survival. BMC Geriatr. 10, 55 (2010).
24. Xue, X. et al. Characterization of the fatty acyl elongase (ELOVL) gene family, and hepatic ELOVL and delta-6 fatty acyl desaturase transcript expression and fatty acid responses to diets containing camelina oil in Atlantic cod (Gadus morhua). Comp. Biochem. Physiol. B Biochem. Mol. Biol. 175, 9-22 (2014).
25. Bartke, A. & Brown-Borg, H. Life extension in the dwarf mouse. Curr. Top. Dev. Biol. 63, 189-225 (2004).
26. Wang, T. et al. Epigenetic aging signatures in mice livers are slowed by dwarfism, calorie restriction and rapamycin treatment. Genome Biol. 18, 57 (2017).
27. Kolesnikov, A. V., Fan, J., Crouch, R. K. & Kefalov, V. J. Age-Related Deterioration of Rod Vision in Mice. J. Neurosci. Off. J. Soc. Neurosci. 30, 11222-11231 (2010).
28. Zadravec, D. et al. ELOVL2 controls the level of n-6 28:5 and 30:5 fatty acids in testis, a prerequisite for male fertility and sperm maturation in mice. J. Lipid Res. 52, 245-255 (2011).
29. Garagnani, P. et al. Methylation of ELOVL2 gene as a new epigenetic marker of age. Aging Cell 11, 1132-1134 (2012).
30. Bacalini, M. G. et al. A meta-analysis on age-associated changes in blood DNA methylation: results from an original analysis pipeline for Infinium 450k data. Aging 7, 97-109 (2015).
31. Hayflick, L. The limited in vitro lifetime of human diploid cell strains. Exp. Cell Res. 37, 614-636 (1965).
32. Herbig, U., Ferreira, M., Condel, L., Carey, D. & Sedivy, J. M. Cellular senescence in aging primates. Science 311, 1257 (2006).
33. Röhme, D. Evidence for a relationship between longevity of mammalian species and life spans of normal fibroblasts in vitro and erythrocytes in vivo. Proc. Natl. Acad. Sci. U.S.A. 78, 5009-5013 (1981).
34. Wang, H. et al. One-Step Generation of Mice Carrying Mutations in Multiple Genes by CRISPR/Cas-Mediated Genome Engineering. Cell 153, 910-918 (2013).
35. Bae, S., Park, J. & Kim, J.-S. Cas-OFFinder: a fast and versatile algorithm that searches for potential off-target sites of Cas9 RNA-guided endonucleases. Bioinformatics 30, 1473-1475 (2014).
36. Luo, J. et al. Human retinal progenitor cell transplantation preserves vision. J. Biol. Chem. 289, 6362-6371 (2014).

What is claimed is:

1. A method for treating, ameliorating or preventing an age-related eye disease or condition comprising administering an effective amount of at least one demethylation agent to a subject in need of treatment.

2. The method of claim 1, wherein the demethylation agent increases the expression of the elongation of very long chain fatty acids-like 2 gene (ELOVL2) and/or increase the level of ELOVL2 enzyme and/or increase the level of retinal 22:6(n-3) docosahexaenoic (DHA) and 22:5(n-6), docosapentaenoic acid (DPA).

3. The method of claim 1, wherein the demethylation agent is selected from 5-azacytidine, decitabine, zebularine, procainamide, procaine, hydralazine, valproic acid and epigallocatechin gallate (EGCG).

4. The method of claim 1, wherein the demethylating agent is administered to the eye.

5. The method of claim 1, wherein the demethylating agent is administered to the eye by an intravitreal, subretinal, subconjunctival, subtenon, or posterior juxtascleral route.

6. The methods of claim 1, wherein the age-related eye disease is age-related macular degeneration (AMD), diabetic eye disease, glaucoma, low vision or dry eye.

7. The method of claim 6, wherein the AMD is dry or wet AMD.

8. The method of claim 7, wherein the AMD is dry AMD.

9. The method of claim 1, wherein the demethylating agent is administered as a time-released formulation.

10. The method of claim 1, wherein the demethylating agent is decitabine.

11. A method comprising selecting a patient in need of treatment of an age-related eye disease and administering an effective amount of one or more demethylating agents to the eye of the patient whereby the age-related disease is treated.

12. The method of claim 11, wherein the patient is selected by determining the methylation of ELOVL2 and/or ELOVL2 expression in the eye of the patient.

13. The method of claim 11, wherein the demethylating agent is decitabine.

14. The methods of claim 11, wherein the age-related eye disease is age-related macular degeneration (AMD), diabetic eye disease, glaucoma, low vision or dry eye.

15. The method of claim 14, wherein the age-related eye disease is dry AMD.

* * * * *